United States Patent [19]
Junge et al.

[11] Patent Number: 5,021,438
[45] Date of Patent: Jun. 4, 1991

[54] 1,3,4,5-TETRAHYDROBENZ(C,D)INDOLES

[75] Inventors: Bodo Junge, Wuppertal; Bernd Richter, Bergisch-Gladbach; Thomas Glaser, Roesrath; Jörg Traber, Lohmar, all of Fed. Rep. of Germany

[73] Assignee: Bayer Aktiengesellschaft, Leverkusen, Fed. Rep. of Germany

[21] Appl. No.: 324,518

[22] Filed: Mar. 15, 1989

[30] Foreign Application Priority Data

Mar. 18, 1988 [DE] Fed. Rep. of Germany ....... 3809155

[51] Int. Cl.$^5$ .................. A61K 31/425; C07D 513/00
[52] U.S. Cl. ..................................... 514/373; 548/209; 548/474; 548/181; 548/217; 548/221; 548/233; 548/235; 548/243; 548/244; 548/245; 548/246; 548/247; 548/249; 548/159; 548/436; 548/213; 548/214; 548/208; 548/207; 548/210; 546/272; 546/16; 546/156; 546/157; 546/167; 546/155; 546/141; 546/146; 546/148; 546/142; 546/143; 546/153; 546/159; 546/171; 546/176; 546/177; 546/200; 544/33; 544/333; 544/3; 544/310; 544/316; 544/319; 544/324; 544/328; 544/331
[58] Field of Search ............... 548/436, 474, 181, 217, 548/221, 233, 235, 243, 244, 245, 246, 247, 249, 159, 213, 214, 208, 207, 210; 514/288, 410, 222.2, 226.5, 269, 272, 278, 309, 310, 307, 312, 313, 320, 366, 373, 376, 377, 374, 380, 378, 372; 544/3, 33, 310, 316, 319, 324, 328, 331, 333; 546/16, 141, 142, 143, 148, 155, 157, 153, 159, 171, 176, 177, 200

[56] References Cited

U.S. PATENT DOCUMENTS 2,809,974 10/1957 Kornyeld .................. 548/436
4,110,339 8/1978 Bach et al. .................. 548/436

FOREIGN PATENT DOCUMENTS 0029581 6/1981 European Pat. Off. .
272534 12/1986 European Pat. Off. ............. 546/16
0207695 1/1987 European Pat. Off. .
293716 7/1988 European Pat. Off. ............. 548/436
3346513 4/1985 Fed. Rep. of Germany ...... 546/200

2471373 10/1979 France .

OTHER PUBLICATIONS

Cassady et al., "Ergot Alkaloids, Ergolines . . . ", J. Med. Chem. 17(3) 300–307 (1974).
Grob et al., "Benz (CD) Indole Series, VIII . . . ", CA 56(7):7285h (1962).

Primary Examiner—Jane T. Fan
Assistant Examiner—Celia Chang
Attorney, Agent, or Firm—Sprung Horn Kramer & Woods

[57] ABSTRACT

Novel compounds having an affinity for 5-hydroxy-tryptamine receptors of the formula

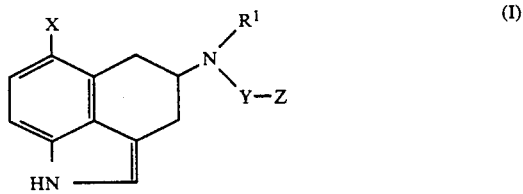

(I)

in which $R^1$ stands for H, alkyl, aralkyl or heteroarylalkyl,
X stands for H, $OCH_3$, OH, $SCH_3$, halogen, CN or $CONH_2$,
Y stands for a straight-chain or branched, saturated or unsaturated alkylene chain having up to 6 carbon atoms
and
Z stands for a group of the formula

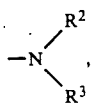

$-OR^4$, $-SO_mR^5$, $-COOR^6$ or $CONR^7R^8$
or salts thereof.

14 Claims, No Drawings

1,3,4,5-TETRAHYDROBENZ(C,D)INDOLES

The invention relates to substituted 1,3,4,5-tetrahydrobenz[c,d]indoles, processes for their preparation and their use in medicaments.

From DE 3,346,573, EP 153,083 and EP 162,695 it is already known that 6-substituted 1,3,4,5-tetrahydrobenz[c,d]indole-4-amines possess a high affinity for serotonin receptors of the 5-HT$_1$ type and can be used for the treatment of diseases.

New 6-substituted 4-amino-1,3,4,5-tetrahydrobenz[c,d]indoles of the general formula (I),

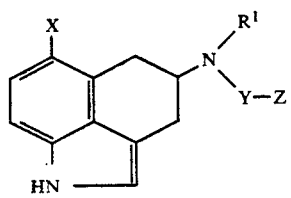

in which
R$^1$ stands for H, alkyl, aralkyl or heteroarylalkyl,
X stands for H, OCH$_3$, OH, SCH$_3$, halogen, CN or CONH$_2$,
Y stands for a straight-chain or branched, saturated or unsaturated alkylene chain having up to 6 carbon atoms
and
Z stands for cyano or for a group of the formula

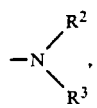

—OR$^4$, —SO$_m$R$^5$, —COOR$^6$ or —CONR$^7$R$^8$
where
R$^4$ stands for hydrogen, alkyl, alkenyl, cycloalkyl, aryl, aralkyl, acyl, alkoxycarbonyl, aryloxycarbonyl or aralkoxycarbonyl
R$^5$ stands for alkyl, alkenyl, cycloalkyl, aryl or aralkyl, where the aryl radicals can be monosubstituted, disubstituted or trisubstituted by identical or different halogen, cyano, alkyl, alkoxy, trifluoromethyl or trifluoromethoxy, or for a group of the formula —NR$^7$R$^8$,
R$^6$ stands for hydrogen, alkyl, alkenyl, cycloalkyl, aryl or aralkyl,
R$^7$ and R$^8$ are identical or different and stand for hydrogen, alkyl, alkenyl, cycloalkyl, aryl or aralkyl,
m stands for a number 0, 1 or 2,
R$^2$ and R$^3$ are identical or different and stand for hydrogen, alkyl, alkenyl, cycloalkyl, aryl or aralkyl, where the aryl radicals can be substituted by halogen, cyano, alkyl, alkoxy or trifluoromethyl, or for a group of the formula —COR$^9$ or —SO$_2$R$^{10}$,
wherein
R$^9$ denotes hydrogen, or a group NHR$^{11}$, or denotes alkyl or alkoxy, or denotes aryl, aralkyl, aralkoxy or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino,
R$^{10}$ denotes alkyl which can be substituted by cyano, halogen, trifluoromethyl, trifluoromethoxy or alkoxycarbonyl, or denotes aryl, aralkyl or heteroaryl, where the radicals mentioned can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino, or denotes a group NR$^7$R$^8$,
where
R$^7$ and R$^8$ have the abovementioned meaning
and
R$^{11}$ denotes alkyl which is optionally substituted by cyano, halogen, trifluoromethyl or trifluoromethoxy, or denotes aryl, aralkyl or heteroaryl, where the aryl radicals can be monosubstituted, disubstituted or trisubstituted by identical or different alkyl, alkoxy, alkylthio, halogen, cyano, trifluoromethyl, trifluoromethoxy, trifluoromethylthio, amino, alkylamino or dialkylamino,
or where
R$^2$ and R$^3$, together with the nitrogen atom, form a heterocyclic ring from the series comprising

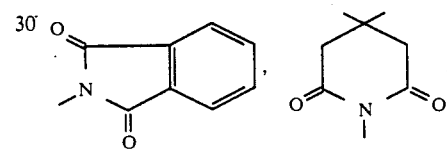

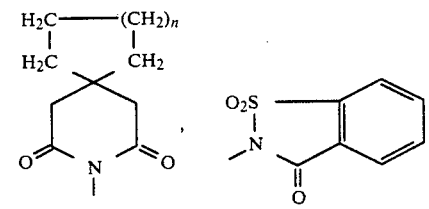

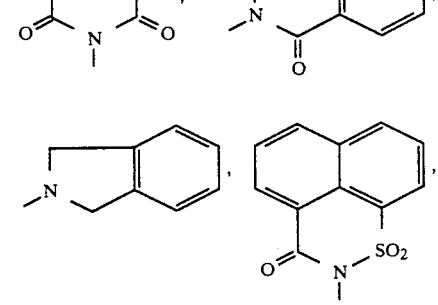

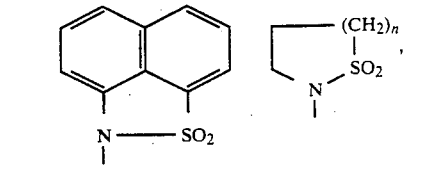

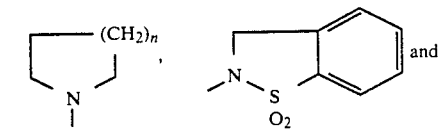

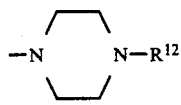

wherein
n denotes a number 1 or 2,
and
R¹² stands for acyl, alkoxycarbonyl, alkylsulphonyl, phenylsulphonyl, tolylsulphonyl, benzylsulphonyl, carbamoyl or sulphamoyl
and their salts, have now been found.

The substances according to the invention have several asymmetric carbon atoms and can therefore exist in different stereochemical forms. Moreover, compounds having a sulphoxide group can likewise exist in different stereochemical forms. The invention relates to both the individual isomers and their mixtures. For example, the following isomeric forms of the 1,3,4,5-tetrahydrobenz[c,d]indoles substituted with bases may be made:

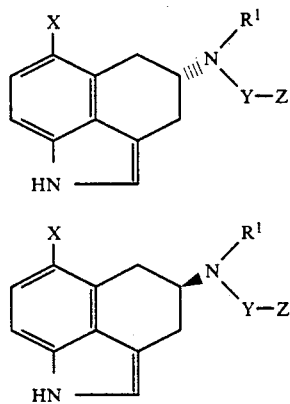

The 1,3,4,5-tetrahydrobenz[c,d]indoles substituted with bases according to the invention can also exist in the form of their salts. In general, salts with inorganic or organic acids may be mentioned here.

In the context of the present invention, physiologically acceptable salts are preferred. Physiologically acceptable salts of the 1,3,4,5-tetrahydrobenz[c,d]indoles substituted with bases can be salts of the substances according to the invention with mineral acids, carboxylic acids or sulphonic acids. For example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, oxalic acid, malonic acid, succinic acid, maleic acid, fumaric acid, malic acid, tartaric acid, citric acid or benzoic acid are particularly preferred.

The substances according to the invention surprisingly show an advantageous action on the central nervous system and can be used for therapeutic treatment of humans and animals. Compared to the already known structurally related compounds, they are distinguished, above all, by a better tolerability.

Alkyl in general stands for a straight-chain or branched hydrocarbon radial having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl in general stands for a straight-chain or branched hydrocarbon radical having 2 to 12 carbon atoms and one or more, preferably having one or two, double bonds. The lower alkenyl radical having 2 to about 6 carbon atoms and one double bond is preferred. An alkenyl radical having 2 to 4 carbon atoms and one double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

Cycloalkyl in general stands for a cyclic hydrocarbon radical having 5 to 8 carbon atoms. The cyclopentane and cyclohexane rings are preferred. Examples which may be mentioned are cyclopentyl, cyclohexyl, cycloheptyl and cyclooctyl.

Aryl in general stands for an aromatic radical having 6 to about 12 carbon atoms. Preferred aryl radicals are phenyl, naphthyl and biphenyl.

Aralkyl in general stands for an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

Alkoxy in general stands for a straight-chain or branched hydrocarbon radical having 1 to 12 carbon atoms which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Aryloxy in general stands for an aromatic radical having 6 to about 12 carbon atoms which is bonded via an oxygen atom. Preferred aryloxy radicals are phenoxy or naphthyloxy.

Aralkoxy in general stands for an aralkyl radical having 7 to 14 carbon atoms, the alkylene chain being bonded via an oxygen atom. Aralkoxy radicals having 1 to 6 carbon atoms in the aliphatic moiety and 6 to 12 carbon atoms in the aromatic moiety are preferred. Examples which may be mentioned are the following aralkoxy radicals: benzyloxy, naphthylmethoxy, phenethoxy and phenylpropoxy.

Acyl in general stands for phenyl or straight-chain or branched lower alkyl having 1 to about 6 carbon atoms which are bonded via a carbonyl group. Phenyl and alkyl radicals having up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Alkoxycarbonyl can be represented, for example, by the formula

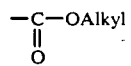

In this connection, alkyl stands for a straight-chain or branched hydrocarbon radical having 1 to 12 carbon atoms. Lower alkoxycarbonyl having 1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Aryloxycarbonyl can be represented, for example, by the formula —COO-aryl. In this connection, aryl in general stands for an aromatic radical having 6 to 12 carbon atoms. Examples which may be mentioned are: phenoxycarbonyl and naphthyloxycarbonyl.

Aralkoxycarbonyl can be represented, for example, by the formula —COO—aralkyl. In this connection, aralkyl in general stands for an aryl radical having 7 to 14 carbon atoms which is bonded via an alkylene chain, aralkyl radicals having 1 to 6 carbon atoms in the aliphatic moiety and 6 to 12 carbon atoms in the aromatic moiety being preferred. For example, aralkoxycarbonyl radicals which may be mentioned are: benzyloxycarbonyl and naphthylmethyloxycarbonyl.

Heteroaryl in the scope of the abovementioned definition in general stands for a 5- to 6-membered aromatic ring which can contain oxygen, sulphur and/or nitrogen as hetero atoms and onto which can be fused a further aromatic ring. 5- and 6-membered aromatic rings which contain one oxygen, one sulphur and/or up to 2 nitrogen atoms and which are optionally fused to benzene are preferred. Heteroaryl radicals which may be mentioned as particularly preferred are: thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl and indolyl.

Halogen in general stands for fluorine, chlorine, bromine or iodine, preferably for fluorine, chlorine or bromine. Particularly preferably, halogen stands for fluorine or chlorine.

Preferred compounds of the general formula (I) are those in which $R^1$ stands for H, $C_1$–$C_4$-alkyl or benzyl, X stands for H, $OCH_3$, OH, $SCH_3$, F, Cl, Br, CN or $CONH_2$, Y stands for a straight-chain or branched, saturated or unsaturated alkylene chain having up to 6 carbon atoms and Z stands for cyano or for a group of the formula

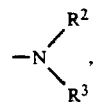

$-SO_2NR^7R^8$ and $CONR^7R^8$ wherein $R^7$ and $R^8$ are identical or different, and stand for hydrogen, lower alkyl, phenyl, benzyl or phenethyl, $R^2$ and $R^3$ are identical or different and stand for hydrogen, lower alkyl, phenyl or benzyl, where the phenyl radicals can be substituted by fluorine, chlorine, bromine, lower alkyl, lower alkoxy or trifluoromethyl, or stand for a group of the formula $-COR^9$ or $-SO_2R^{10}$, wherein $R^9$ denotes hydrogen or a group $NHR^{11}$, or denotes lower alkyl or lower alkoxy, or denotes phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl, each of which is optionally substituted by lower alkyl, lower alkoxy, fluorine, chlorine, bromine, trifluoromethyl, dimethylamino or diethylamino, $R^{10}$ denotes lower alkyl which is optionally substituted by cyano, fluorine, chlorine, bromine, trifluoromethyl or lower alkoxycarbonyl, or denotes phenyl, naphthyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl, each of which is optionally substituted by lower alkyl, lower alkoxy, fluorine, chlorine, bromine, trifluoromethyl, dimethylamino or diethylamino, or denotes a group $NR^7R^8$, where $R^7$ and $R^8$ have the abovementioned meaning, and $R^{11}$ denotes lower alkyl which is optionally substituted by cyano, fluorine, chlorine or bromine, or denotes phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl, each of which is optionally substituted by lower alkyl, lower alkoxy, fluorine, chlorine, bromine, trifluoromethyl, dimethylamino or diethylamino, or $R^2$ and $R^3$, together with the nitrogen atom, form a heterocyclic ring from the series comprising

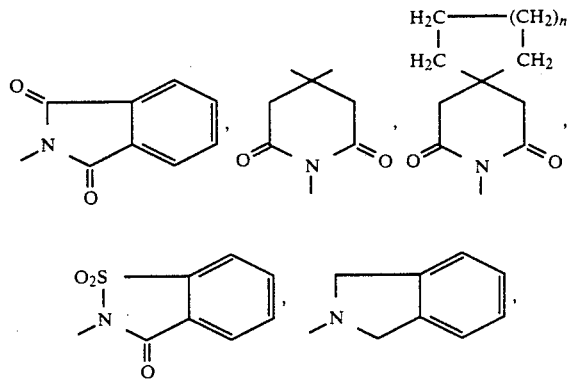

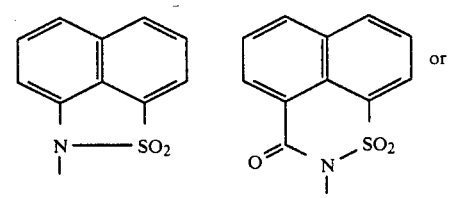

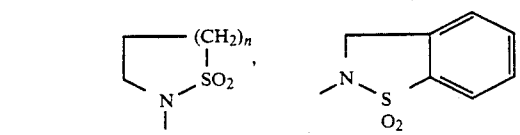

wherein n denotes a number 1 or 2 and their salts.

Particularly preferred compounds of the formula (I) are those in which $R^1$ stands for H, CH₃, ethyl, n-propyl or benzyl, X stands for H, OCH₃, OH, SCH₃, F, Cl, CN or CONH₂, Y stands for a straight-chain alkylene chain having 2 to 4 carbon atoms and Z stands for Cyano or for a group of the formula $$-N\begin{matrix}R^2\\R^3\end{matrix}$$

—SO₂NR⁷R⁸ or —CONR⁷R⁸
where $R^7$ and $R^8$ are identical or different and stand for hydrogen, methyl, ethyl, propyl, isopropyl, butyl, isobutyl or tert.butyl, $R^2$ and $R^3$ are identical or different, and stand for hydrogen, methyl, ethyl, propyl, isopropyl, butyl, isobutyl, tert.butyl or stand for phenyl which is optionally substituted by fluorine, chlorine, methyl or methoxy, or for a group —COR⁹ or —SO₂R¹⁰, wherein $R^9$ denotes hydrogen or a group NHR¹¹, or denotes methyl, ethyl, propyl, isopropyl, methoxy, ethoxy, propoxy, isopropoxy, or phenyl, benzyl, benzyloxy, thienyl, furyl, pyridyl, pyrimidyl, quinolyl or isoquinolyl, each of which is optionally substituted by methyl, methoxy, fluorine or chlorine, $R^{10}$ denotes methyl, ethyl, propyl, isopropyl, butyl or isobutyl, each of which is optionally substituted by fluorine, chlorine, methoxycarbonyl, ethoxycarbonyl, propoxycarbonyl, isopropoxycarbonyl, butoxycarbonyl or isobutoxycarbonyl, or denotes phenyl, naphthyl, benzyl, thienyl, furyl, pyridyl, pyrimidyl, quinolyl or isoquinolyl, each of which is optionally substituted by methyl, ethyl, propyl, isopropyl, methoxy, fluorine or chlorine, or denotes a group NR⁷R⁸, where $R^7$ and $R^8$ have the abovementioned meaning, and $R^{11}$ denotes methyl, ethyl, propyl, isopropyl, butyl, isobutyl, pentyl, isopentyl, hexyl or isohexyl, each of which is optionally substituted by fluorine or chlorine, or denotes phenyl or benzyl, each of which can be substituted by fluorine, chlorine, methyl or methoxy, or $R^2$ and $R^3$, together with the nitrogen atom, form a heterocyclic ring from the series comprising wherein
n denotes a number 1 or 2
and their salts.

Compounds according to the invention which may be mentioned by way of example are:

6-methoxy-4-[4-(N-1,2-benzisothiazol-3(2H)-one-1,1-dioxide-yl])-butylamino-1,3,4,5-tetrahydrobenz[c,d]indole hydrochloride, 4-[4-(N-1,2-benzisothiazol-3(2H)-one-1,1-dioxide-yl)]-butylamino-1,3,4,5-tetrahydrobenz[c,d]indole, 6-methoxy-4-[N-propyl-N-(ethyloxycarbonylaminoethyl)]-amino-1,3,4,5-tetrahydrobenz[c,d]indole, 6-methoxy-4-[N-propyl-N-(methylsulphonylamidoethyl)]-amino-1,3,4,5-tetrahydrobenz[c,d]indole, 6-methoxy-4-[N-propyl-N-(butylsulphonylamidoethyl)]-amino-1,3,4,5-tetrahydrobenz[c,d]indole, 6-methoxy-4-[N-propyl-N-tosylamidoethyl)]-amino-1,3,4,5-tetrahydrobenz[c,d]indole hydrochloride, 6-methoxy-4-[N-propyl-N-(2-naphthylsulphonylamidoethyl)]-amino-1,3,4,5-tetrahydrobenz[c,d]indole hydrochloride, 6-methoxy-4-[N-propyl-N-(1-phenylureidoethyl)]-amino-1,3,4,5-tetrahydrobenz[c,d]indole, 6-methoxy-4-(dimethylsulphamoylethyl)-amino-1,3,4,5-tetrahydrobenz[c,d]indole, 6-methoxy-4-[N-propyl-N-(dimethylsulphamoylethyl)]-amino-1,3,4,5-tetrahydrobenz[c,d]indole, 6-methoxy-4-(methylsulphonylamidopropyl)-amino-1,3,4,5-tetrahydrobenz[c,d]indole hydrochloride, 6-methoxy-4-[N-benzyl-N-(methylsulphonylamidopropyl)]-amino-1,3,4,5-tetrahydrobenz[c,d]indole, 6-methoxy-4-(4-fluorophenylsulphonylamidopropyl)-amino-1,3,4,5-tetrahydrobenz[c,d]indole hydrochloride, 6-methoxy-4-[N-benzyl-N-(4-fluorophenylsulphonylamidopropyl)]-amino-1,3,4,5-tetrahydrobenz[c,d]indole.

It has furthermore been found that compounds of the formula (I) are obtained by reductive amination [A] of ketones of the formula (II)

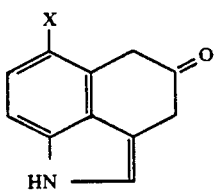
(II)

in which X has the abovementioned meaning, with amines of the formula (III), (IV) or (V)

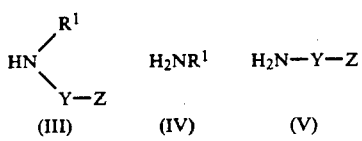

in which $R^1$, Y and Z have the abovementioned meanings.

In addition, compounds of the general formula (I) are obtained when compounds of the general formula (VI)

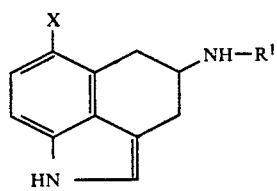
(VI)

in which $R^1$ and X have the abovementioned meanings, are reacted [B] with alkylating agents of the formula (VII)

 (VII)

in which Y and Z have the abovementioned meanings, and L denotes a leaving group customary in alkylating agents, such as Cl, Br, I, OTs, OMs or $OSO_2CF_3$, or reductively alkylated [C] with aldehydes of the formula (VIII)

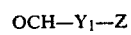 (VIII)

in which Z has the abovementioned meaning and $Y^1$ is an alkylene chain Y shortened by one methylene group, or reacted with reactive acid derivatives of the general formula (IX)

 (IX)

in which $Y^1$ and Z have the abovementioned meanings and M denotes a leaving group customary in acylating agents, such as chlorine, bromine, alkoxy, aryloxy, imidazolyl, thiazolyl, methanesulphonyloxy or alkoxycarbonyloxy, and the acid amides obtained are reduced [D] catalytically with hydrogen or with complex metal hydrides to give compounds of the formula (I).

Compounds of the formula (I) are also obtained when compounds of the formula (X)

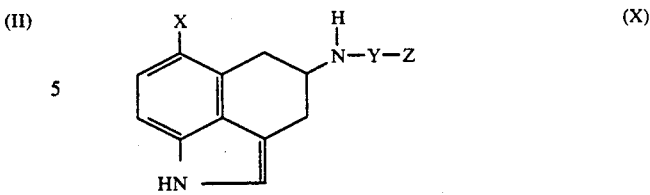
(X)

in which X, Y and Z have the abovementioned meanings, are alkylated [E] with alkylating agents of the formula (XI)

 (XI)

in which $R^1$ and L have the abovementioned meanings, or reductively alkylated [F] with aldehydes of the formula (XII)

 (XII)

in which $R^{13}$ is a radical $R^1$ shortened by one methylene group, or reacted with reactive acid derivatives of the general formula (XIII)

 (XIII)

in which $R^{13}$ and M have the abovementioned meanings, and the acid is obtained are reduced [G] catalytically with hydrogen or with complex metal hydrides to give compounds of the formula (I).

In addition, compounds of the formula (I) are obtained from compounds of the formula (VI) by first reacting the latter stepwise by alkylation or reductive alkylation to give intermediates having suitable functional groups and then converting [H] these intermediates into compounds of the formula (I) by modification of the functional groups by oxidation, reduction, hydrolysis or reaction with electrophilic reagents.

For example, the compounds of the formula (VI)

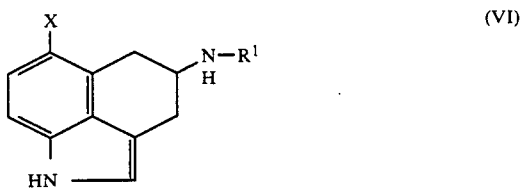
(VI)

in which X and $R^1$ have the abovementioned meanings, are alkylated with chloroacetonitrile or acrylonitrile to give compounds of the formulae (XIV) and (XV)

 (XIV)

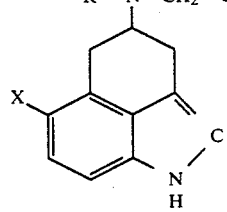

-continued

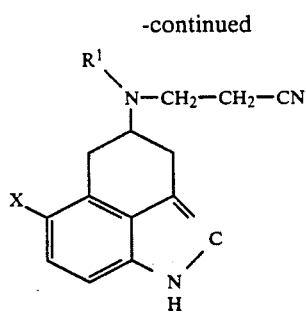
(XV)

the nitriles obtained rae hydrogenated to give the amines (XVI) and (XVII)

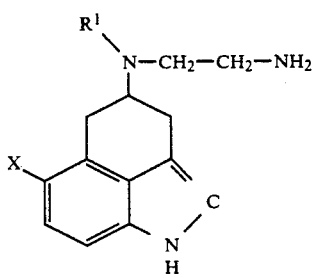
(XVI)

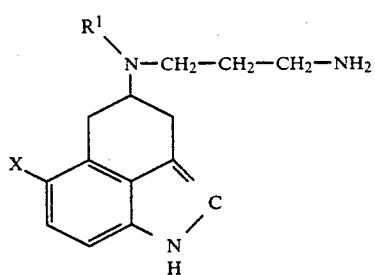
(XVII)

and these are converted into compounds of the formula (I) according to the invention in a manner known per se by alkylation, reductive alkylation, acylation, reaction with isocyanates or sulphonylation.

The following reaction schemes serve to illustrate by way of example the processes for the preparation of compounds of the formula (I).

Process A

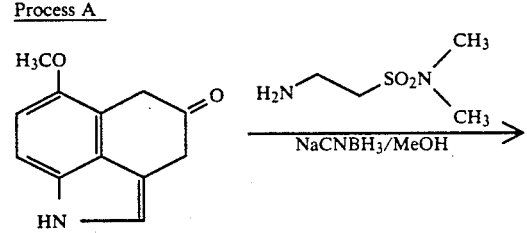

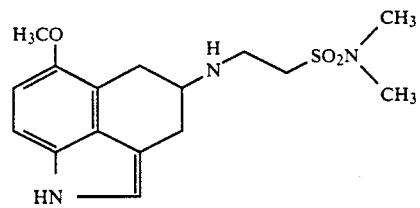

-continued

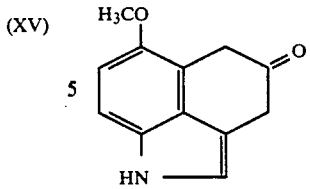

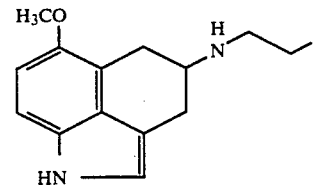

Process B

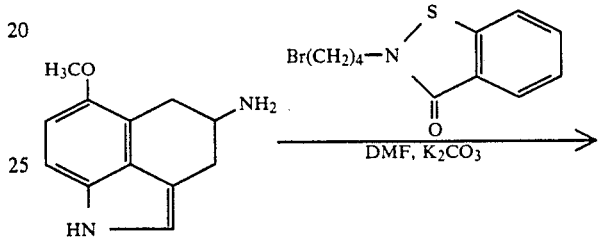

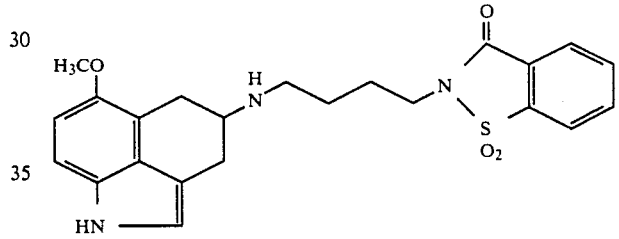

Process C

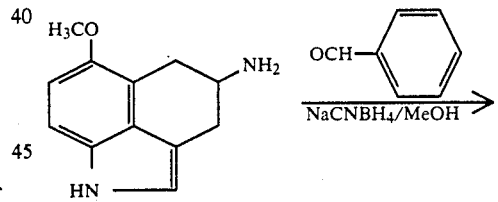

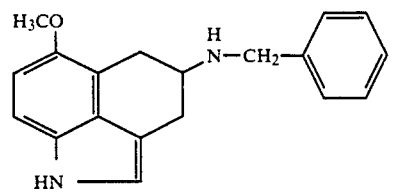

Process D

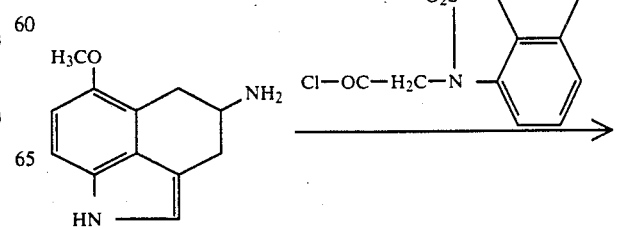

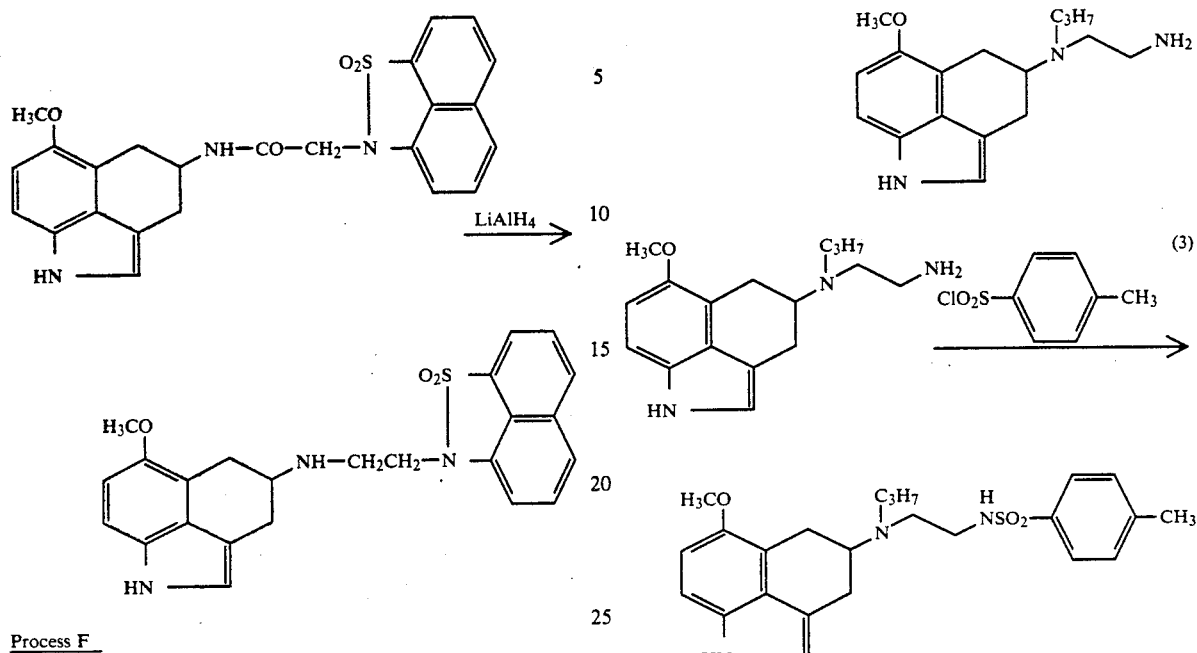
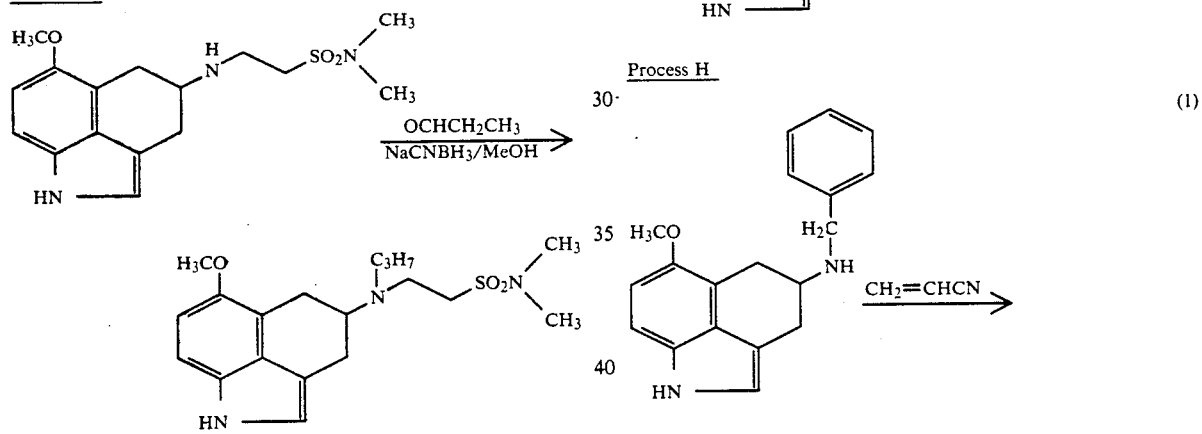
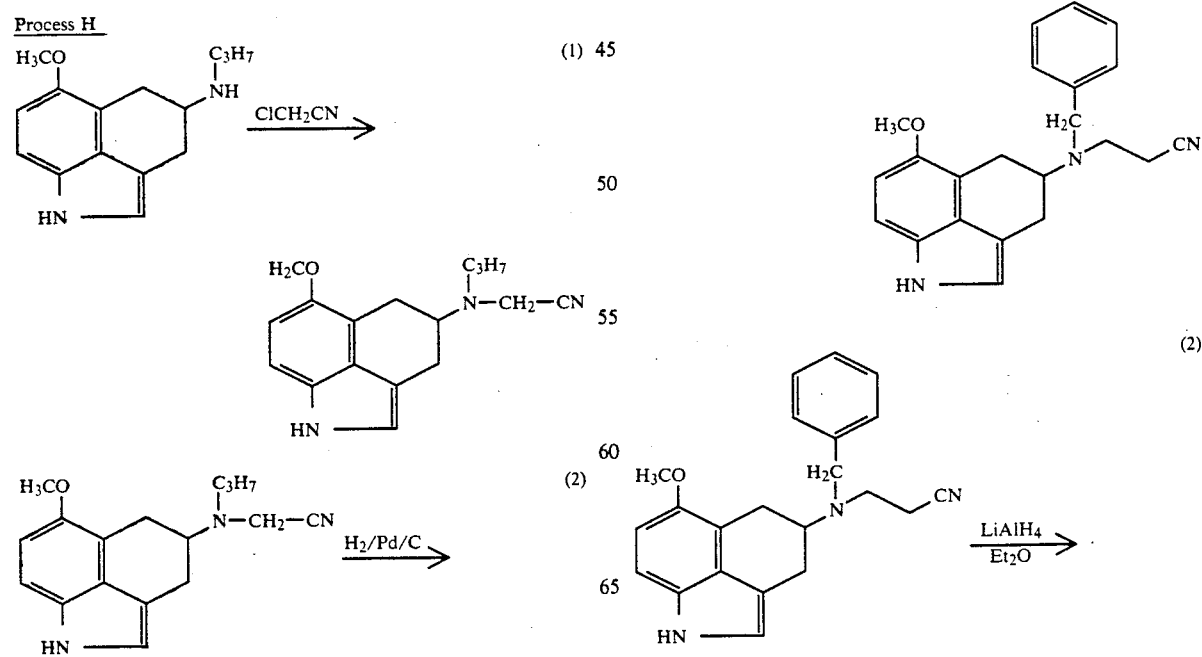

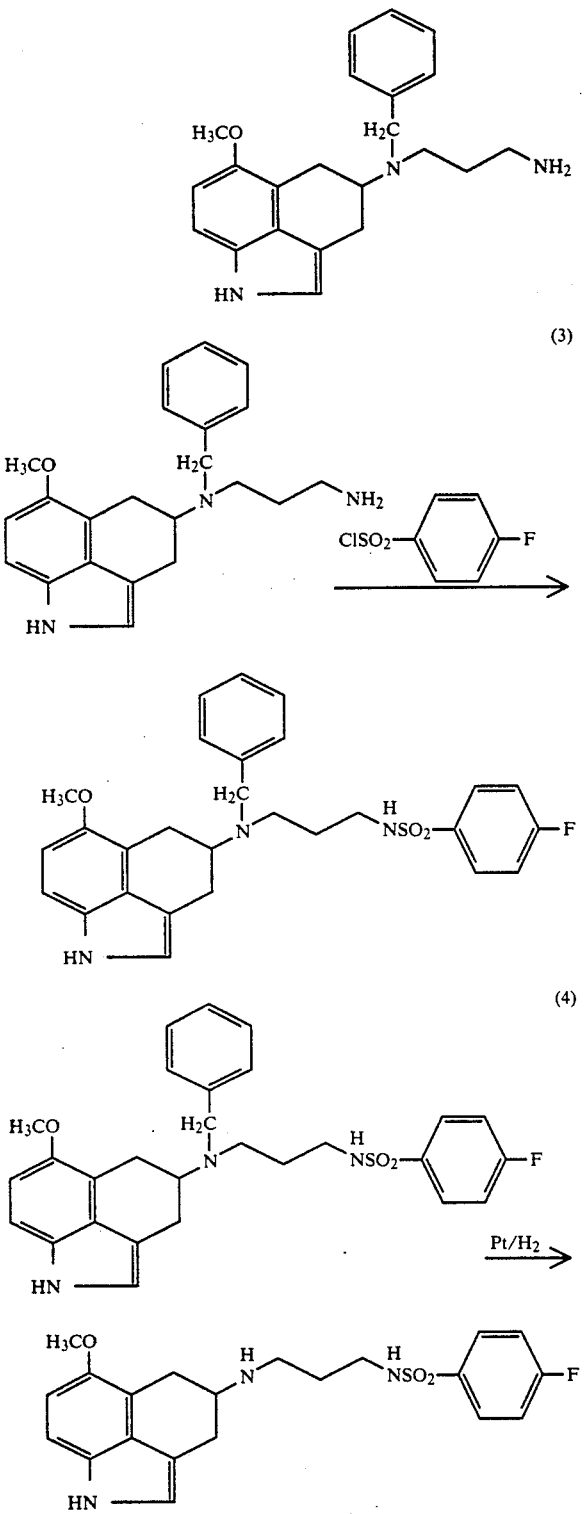

The ketones of the general formula (II) used as starting materials are known or can be prepared by known methods [EP 0,162,695 and EP 0,153,083].

The amines of the general formula (III), (IV) and (V) used as starting materials are known or can be prepared by known methods [Houben-Weyl's "Methoden der organischen Chemie" ("Methods of Organic Chemistry") volume XI/1 and XI/2].

The preparation of the Schiff's bases or enamines by reaction of the tetralones (II) with amines (III) takes place in inert organic solvents, if appropriate in the presence of a catalyst and if appropriate in the presence of a water-binding agent.

The process according to the invention can be carried out in two steps, i.e. with isolation of the enamines. It is similarly possible to carry out the process according to the invention as a one-pot process.

Inert solvents which are suitable in this case are the customary organic solvents which do not change under the reaction conditions. These preferably include alcohols such as methanol, ethanol, propanol or isopropanol, or ethers such as diethyl ether, butyl methyl ether, dioxane, tetrahydrofuran, glycol dimethyl ether or diethylene glycol dimethyl ether, or halogenated hydrocarbons such as, for example, methylene chloride, chloroform or carbon tetrachloride, or hydrocarbons such as benzene, toluene, xylene, or mineral oil fractions, or amides such as dimethylformamide or hexamethylphosphoric triamide, or acetic acid. In addition, it is possible to use mixtures of the solvents mentioned.

In general, acids are used as catalysts. These preferably include inorganic acids such as, for example, hydrochloric acid or sulphuric acid, or organic sulphonic or carboxylic acids such as, for example, methanesulphonic acid, ethanesulphonic acid, benzenesulphonic acid, toluenesulphonic acid, acetic acid or propionic acid.

The water formed in the reaction can be removed, if desired, mixed with the solvent used during or after the reaction, for example by distillation or by addition of water-binding agents, such as, for example, phosphorus pentoxide or preferably by molecular sieve.

The reaction is in general carried out in a temperature range from 0° C. to +150° C., preferably from +20° C. to +100° C.

The reaction can be carried out at atmospheric, elevated and at reduced pressure (for example 0.5–5 bar). In general, the reaction is carried out at atmospheric pressure.

When carrying out the reaction, the starting substances are in general employed in a molar ratio of tetralone (II) to amine (III) of 0.5:2 to 1:1. Molar amounts of the reactants are preferably used.

The reduction of the enamines either takes place by means of hydrogen in water or inert organic solvents such as alcohols, ethers or halogenated hydrocarbons, or their mixtures, using catalysts such as Raney nickel, palladium, palladium on animal charcoal or platinum, or else using hydrides in inert solvents, if appropriate in the presence of a catalyst.

Preferably, the reaction is carried out using hydrides, such as complex borohydrides or aluminum hydrides. Sodium borohydride, lithium aluminum hydride or sodium cyanoborohydride are particularly preferably employed in this case.

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, or amides such as hexamethylphosphoric triamide, or dimethylformamide or acetic acid. It is likewise possible to use mixtures of the solvents mentioned.

Acids are in general used as catalysts in the reduction with sodium cyanoborohydride. These preferably include inorganic acids such as, for example, hydrochloric acid or sulphuric acid or organic carboxylic acids or sulphonic acids, such as, for example, acetic acid, trifluoroacetic acid, trichloroacetic acid, methanesulphonic acid, ethanesulphonic acid, benzenesulphonic acid or toluenesulphonic acid.

When carrying out the process according to the invention, it has proved favorable to carry out the reaction of the tetralones (II) with the amines (III) as a one-pot process in an inert solvent, preferably in ethyl acetate or in alcohols such as, for example, methanol, ethanol, propanol or isopropanol, or their mixtures in the presence of a reducing agent, preferably complex hydrides such as, for example, sodium borohydride or sodium cyanoborohydride, if appropriate in the presence of a dehydrating agent, preferably molecular sieve.

In this case, the reaction is carried out at atmospheric pressure in a temperature range from 0° C. to +150° C., preferably from 0° C. to +100° C. It is likewise possible to carry out the reaction at underpressure or at overpressure (for example in a bomb tube).

If the process according to the invention is carried out as a one-pot reaction, it has proved favorable to employ the amine in an excess of up to 10-fold, preferably in an excess of up to 5-fold, over the tetralone.

The amines of the formula (VI) and (X) are known (EP 0,162,695 and EP 0,153,083) or can be prepared by known processes from the ketones of the formula (II) or amines of the formula (VI) ($R^1$=H) by reductive amination, or by alkylation or reductive alkylation.

The customary organic solvents, which do not change under the reaction conditions, can be used here as solvents for the reaction of the amines (VI) and (X) with the alkylating agents (VII) and (XI). These preferably include alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoric triamide, or dimethyl sulphoxide, acetonitrile, ethyl acetate, or halogenated hydrocarbons such as methylene chloride, chloroform or carbon tetrachloride, or pyridine, picoline or N-methylpiperidine. Mixtures of the solvents mentioned can likewise be used.

Suitable bases are the customary inorganic or organic bases. These preferably include alkali metal hydroxides such as, for example, sodium hydroxide or potassium hydroxide, or alkali metal carbonates such as sodium carbonate or potassium carbonate, or alkali metal alkoxides such as, for example, sodium methoxide or potassium methoxide, or sodium ethoxide or potassium ethoxide, or organic amines such as triethylamine, picoline or N-methylpiperidine, or amides such as sodium amide or lithium diisopropylamide, or organometallic compounds such as butyllithium or phenyllithium.

The reaction is in general carried out in a temperature range from 0° C. to +150° C., preferably from room temperature to +80° C.

The reaction is in general carried out at atmospheric pressure. However, it is likewise possible to carry out the reaction at elevated or reduced pressure.

Alkali metal iodides, preferably sodium iodide or potassium iodide, are in general employed as reaction accelerators.

The base in this connection is employed in an amount from 1 to 5, preferably from 1 to 2, moles relative to 1 mole of the halogen compound. The halogen compound is preferably employed in an excess of up to 10-fold, preferably in an excess of up to 5-fold, over the alkyl-substituted 2-aminotetralin (Ib).

The reductive alkylation of the amines (VI) and (X) with the aldehydes (VIII) and (XII) in general takes place in one step. If the amine (VI) is a primary amine, the reaction can also be carried out as two steps, a Schiff's base or an enamine being obtained first.

The preparation of the Schiff's bases or enamines in the first step takes place in inert organic solvents, if appropriate in the presence of a catalyst and if appropriate in the presence of a water-binding agent. The process according to the invention can be carried out in 2 steps, i.e. with isolation of the intermediates. It is likewise possible to carry out the reduction as a one-pot process.

The customary organic solvents which do not change under the reaction conditions are suitable as inert solvents in this connection. These preferably include alcohols such as methanol, ethanol, propanol or isopropanol, or ethers such as diethyl ether, butyl methyl ether, dioxane, tetrahydrofuran, glycol dimethyl ether or diethylene glycol diethyl ether, or halogenated hydrocarbons such as, for example, methylene chloride, chloroform or carbon tetrachloride, or hydrocarbons such as benzene, toluene, xylene, or mineral oil fractions, or amides such as dimethylformamide or hexamethylphosphoric triamide or acetic acid. In addition, it is possible to use mixtures of the solvents mentioned.

Protonic acids are in general used as catalysts. These preferably include inorganic acids such as, for example, hydrochloric acid or sulphuric acid, or organic carboxylic acids having 1-6 C-atoms, if appropriate substituted by fluorine, chlorine and/or bromine, such as, for example, acetic acid, trifluoroacetic acid, trichloroacetic acid or propionic acid, or sulphonic acids having $C_1$-$C_4$-alkyl radicals or having aryl radicals such as, for example, methanesulphonic acid, ethanesulphonic acid, benzenesulphonic acid or toluenesulphonic acid.

The water formed in the reaction can be removed, if desired, mixed with the solvent used during or after the reaction, for example by distillation or by addition of water-binding agents, such as, for example, phosphorus pentoxide or, preferably by molecular sieve.

The reaction is in general carried out in a temperature range from 0° C. to 150° C., preferably from +20° C. to +100° C.

The reaction can be carried out at atmospheric, elevated and at reduced pressure (for example 0.5-5 bar). In general, the reaction is carried out at atmospheric pressure.

When carrying out the reaction, the compound (V) is employed in an amount of 0.1-10, preferably of 0.5-5, moles relative to 1 mole of monosubstituted basic 2-aminotetralin (Ic).

The reduction of the Schiff's bases or enamines in the second step either takes place by means of hydrogen in water or in inert organic solvents such as alcohols, ethers or halogenated hydrocarbons, or their mixtures, with catalysts such as Raney nickel, palladium, palladium on animal carbon or platinum, or with hydrides in inert solvents, if appropriate in the presence of a catalyst.

Preferably, the reaction is carried out using hydrides, such as complex borohydrides or aluminum hydrides. Sodium borohydride, lithium aluminum hydride or sodium cyanoborohydride are particularly preferably employed in this connection.

All inert organic solvents which do not change under the reaction conditions are suitable as solvents in this connection. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoric triamide or dimethylformamide, or acetic acid. It is likewise possible to use mixtures of the solvents mentioned.

Protonic acids are in general used as catalysts in the reduction using sodium cyanoborohydride. These preferably include inorganic acids such as, for example, hydrochloric acid or sulphuric acid, or organic carboxylic acids having 1-6 C-atoms, if appropriate substituted by fluorine, chlorine and/or bromine, such as, for example, acetic acid, trifluoroacetic acid, trichloroacetic acid or propionic acid, or sulphonic acids having $C_1$-$C_4$-alkyl radicals or having aryl radicals such as, for example, methanesulphonic acid, ethanesulphonic acid, benzenesulphonic acid or toluenesulphonic acid.

When carrying out the process according to the invention, it has proved favorable to carry out the reaction of the aldehydes (VIII) and (XII) with the amines (VI) and (X) as a one-pot process in an inert solvent, preferably in acetic acid or alcohols such as, for example, methanol, ethanol, propanol or isopropanol or their mixtures, in the presence of inorganic or organic acids such as, for example, hydrochloric acid or acetic acid, and in the presence of a reductant, preferably of complex hydrides such as, for example, sodium borohydride or sodium cyanoborohydride, if appropriate in the presence of a dehydrating agent, preferably molecular sieve.

In this case, the reaction is carried out at atmospheric pressure in a temperature range from 0° C. to +150° C., preferably from 0° C. to +100° C. It is likewise possible to carry out the reaction at underpressure or at overpressure (for example in a bomb tube).

The conversion of functional groups into other functional groups in the abovementioned preparation processes takes place, depending on the type of the functional groups, by oxidation, reduction, hydrolysis or by reaction with electrophilic reagents and is illustrated in the following description:

1. The reduction of the nitrile group to the amino group in general takes place using metal hydrides, preferably using lithium aluminum hydride, aluminum hydride (prepared, for example, by reaction of lithium aluminum hydride with 100% strength sulphuric acid or with aluminum chloride) or their mixtures in inert solvents such as ethers or chlorinated hydrocarbons, preferably in ethers such as, for example, tetrahydrofuran, diethyl ether or dioxane in a temperature range from −20° C. to +100° C., preferably from 0° C. to +50° C. at atmospheric pressure.

The reduction is additionally possible by hydrogenating the nitriles in inert solvents such as alcohols, for example methanol, ethanol, propanol or isopropanol in the presence of a noble metal catalyst such as platinum, palladium, palladium on animal carbon or Raney nickel, in a temperature range from 0° C. to +150° C., preferably from room temperature to +100° C. at atmospheric pressure or at overpressure.

The reaction can be illustrated by the following equation:

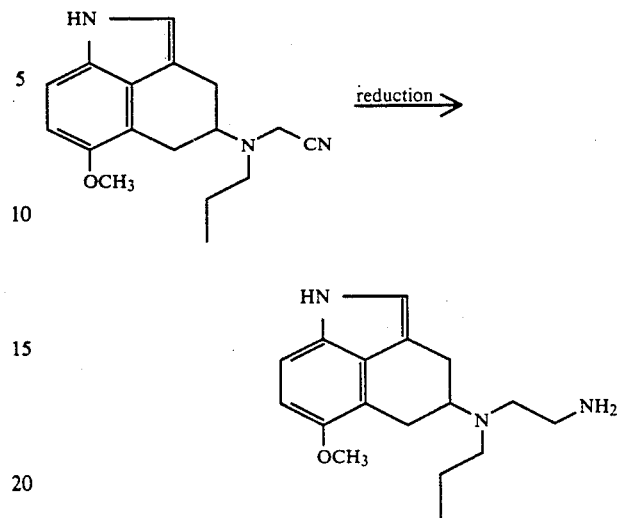

2. The reduction of alkoxycarbonyl groups to alcohol groups in general takes place using hydrides, preferably using lithium aluminum hydride in inert solvents such as ethers, hydrocarbons or halogenated hydrocarbons or their mixtures, preferably in ethers such as, for example, diethyl ether, tetrahydrofuran or dioxane in a temperature range from 0° C. to +150° C., preferably from +20° C. to +100° C. at atmospheric pressure.

The reaction can be illustrated by the following equation:

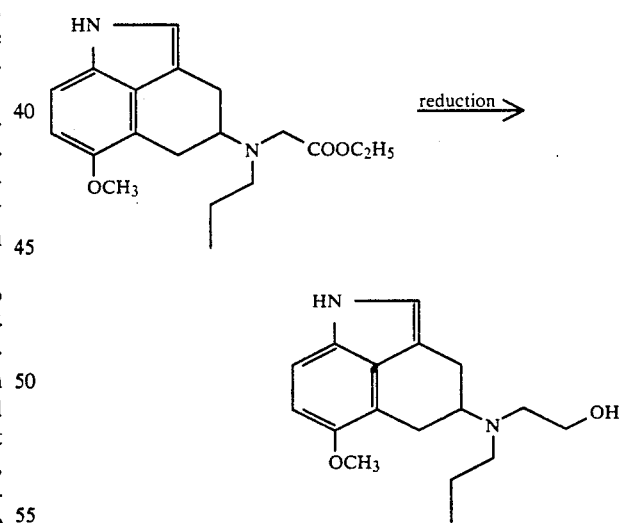

3. The hydrolysis of the nitrile group to the carboxamide group in general takes place with the aid of strong mineral acids, preferably using hydrogen chloride in inert solvents such as water and/or alcohols such as, for example, methanol, ethanol, propanol or isopropanol in a temperature range from 0° C. to +150° C., preferably from +20° C. to +100° C. at atmospheric pressure.

The reaction can be illustrated by the following equation:

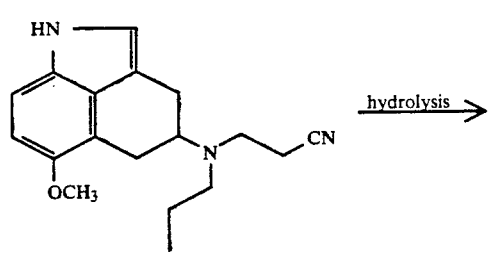

hydrolysis →

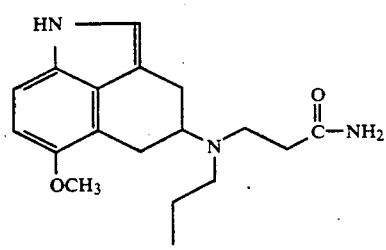

4. By the reaction of NH- or OH-acidic compounds (Z in formula (I) is OH or NR²R³, where R² is H and R³ is H, alkyl, aryl or aralkyl) with electrophilic reagents, a large number of additional compounds according to the invention are obtained:

a) The conversion of amines into carboxamides in general takes place by reaction with carboxylic acid esters in inert solvents such as ethers or their mixtures or hydrocarbons, preferably in ethers such as, for example, diethyl ether, tetrahydrofuran or dioxane, if appropriate in the presence of bases such as alkali metals, alkali metal hydrides, alkali metal alkoxides or organolithium compounds, preferably in the presence of alkali metals such as, for example, sodium or alkali metal hydrides such as sodium hydride or potassium hydride in a temperature range from +20° C. to +150° C., preferably at the boiling point of the solvent used at atmospheric pressure.

Moreover, it is possible to prepare the amides using carboxylic acid halides or anhydrides, preferably using carboxylic acid chlorides in inert solvents such as ethers, hydrocarbons or halogenated hydrocarbons or their mixtures, preferably in ethers such as, for example, diethyl ether, tetrahydrofuran, or halogenated hydrocarbons such as methylene chloride or chloroform, if appropriate in the presence of bases such as alkali metal carbonates, for example sodium carbonate or potassium carbonate, or organic amines such as, for example, triethylamine or pyridine, in a temperature range from −20° C. to +100° C., preferably from 0° C. to +60° C. at atmospheric pressure.

The reaction can be illustrated by the following equation:

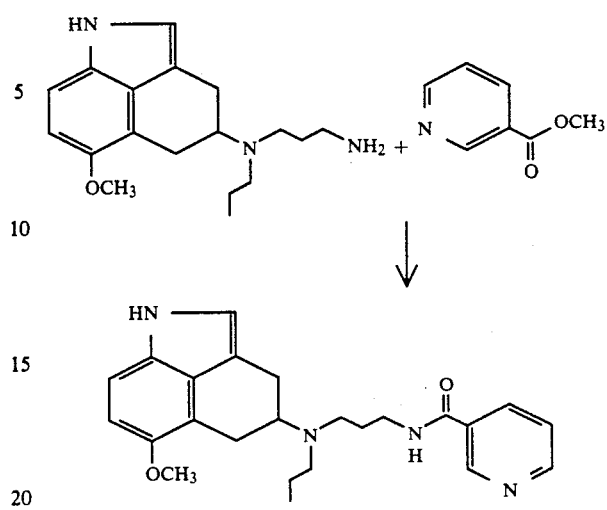

The conversion of amines into carbamates in general takes place using carbonic acid esters, preferably using carbonic acid esters which carry a phenyl ester radical or using chlorocarbonic acid esters, in inert solvents such as ethers, hydrocarbons or halogenated hydrocarbons or their mixtures, preferably in ethers such as, for example, diethyl ether, tetrahydrofuran or dioxane, in a temperature range from +20° C. to +150° C., preferably from +20° C. to +100° C. at atmospheric pressure. The reaction can also be carried out in a two-phase system, where the aqueous phase contains an auxiliary base such as sodium carbonate or potassium carbonate or sodium hydrogen carbonate or potassium hydrogen carbonate.

The reaction can be illustrated by the following equation:

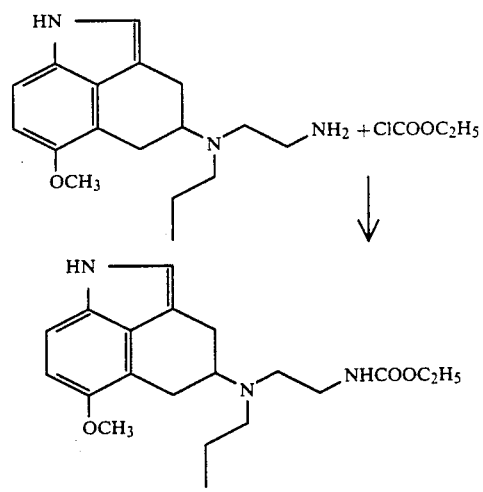

c) The conversion of amines into ureas in general takes place by reaction with isocyanates in inert solvents such as ethers, hydrocarbons or halogenated hydrocarbons or their mixtures, preferably in ethers such as, for example, diethyl ether or tetrahydrofuran, or in halogenated hydrocarbons such as, for example, methylene chloride or chloroform, in a temperature range from −20° C. to +150° C., preferably from 0° C. to +100° C. at atmospheric pressure.

The reaction can be illustrated by the following equation:

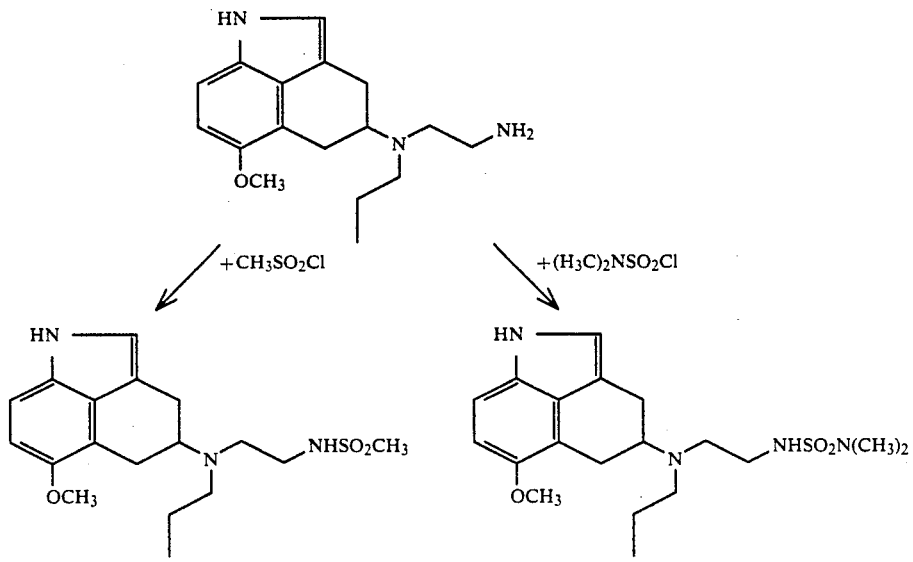

The reaction can be illustrated by the following equation:

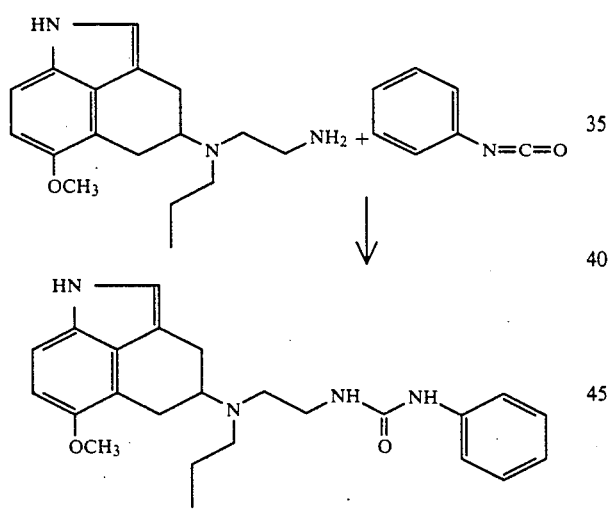

d) The conversion of amines into sulphonamides or aminosulphamoyl derivatives in general takes place using sulphonyl halides or using amidosulphonyl halides, preferably using the corresponding chlorides in inert solvents such as ethers, hydrocarbons or halogenated hydrocarbons or their mixtures, preferably in halogenated hydrocarbons such as, for example, methylene chloride or chloroform, if appropriate in the presence of bases such as alkali metal hydroxides, alkali metal carbonates, alkali metal alkoxides or organic amines, preferably using alkali metal hydroxides such as sodium hydroxide or potassium hydroxide, alkali metal carbonates such as, for example, sodium carbonate or potassium carbonate, or organic amines such as triethylamine or pyridine, in a temperature range from −20° C. to +100° C., preferably from 0° C. to +50° C. at atmospheric pressure.

e) The conversion of the hydroxyl group to carbonic acid esters in general takes place by reacting with halogenoformic acid esters, preferably with chloroformic acid esters in inert solvents such as ethers, hydrocarbons or halogenated hydrocarbons, preferably in halogenated hydrocarbons such as methylene chloride or chloroform, or in ethers such as diethyl ether or tetrahydrofuran, if appropriate in the presence of bases such as alkali metal hydroxides, alkali metal carbonates or organic amines, preferably in the presence of organic amines such as triethylamine, pyridine, picoline or dimethylaminopyridine in a temperature range from −20° C. to +100° C., preferably from 0° C. to room temperature at atmospheric pressure.

The reaction can be illustrated by the following equation:

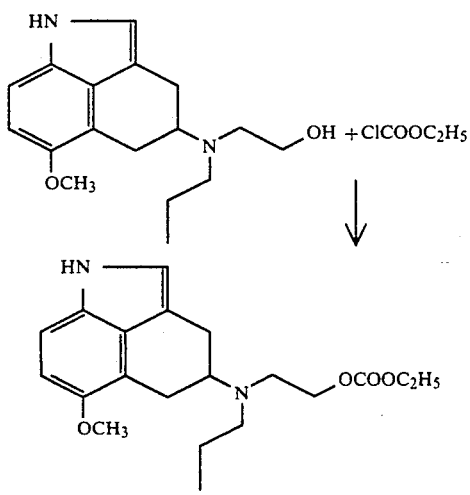

f) Cyclic sulphonamides are in general prepared by reaction of intramolecular electrophiles in inert dipolar aprotic solvents, preferably in dimethylformamide, hexamethylphosphoric triamide or dimethyl sulphoxide, if appropriate in the presence of bases such as alkali metals, alkali metal hydrides, alkali metal amides, alkali metal alkoxides or organolithium compounds, preferably in the presence of alkali metal hydrides such as sodium hydride or potassium hydride, or alkali metal amides such as sodium amide or lithium diisopropylamide, if appropriate in the presence of catalytic amounts of an alkali metal iodide, for example sodium iodide or potassium iodide, in a temperature range from −20° C. to +100° C., preferably from 0° C. to +50° C. at atmospheric pressure.

The reaction can be illustrated by the following equation:

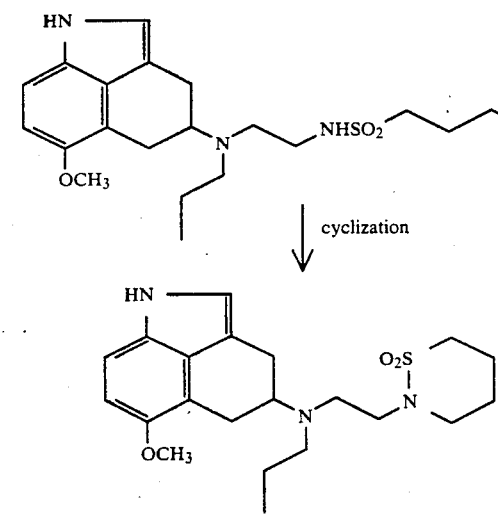

5. The oxidation of the thioether groups to sulphoxides or sulphones in general takes place using oxidants such as peroxo compounds or hydrogen peroxide itself, preferably using hydrogen peroxide, in inert solvents such as carboxylic acids and carboxylic acid anhydrides, preferably in acetic acid, in a temperature range from −20° C. to +100° C., preferably from 0° C. to +50° C.

The reaction can be illustrated by the following equation:

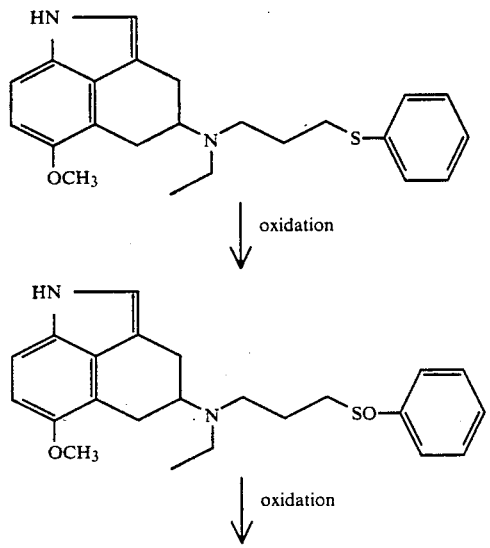

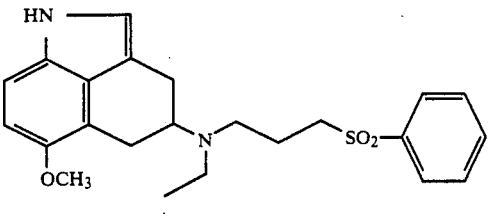

The amines of the general formula (III), (IV) and (V) employed as starting materials are known or can be prepared by known methods [Houben-Weyl's "Methoden der organischen Chemie" ("Methods of Organic Chemistry"), Vol. XI/1 and XI/2].

Amines which can be used, for example, according to the invention are: ammonia, methylamine, ethylamine, propylamine, isopropylamine, butylamine, 4-dimethylaminobutylamine, 4-diethylaminobutylamine, 3-dimethylaminopropylamine, 3-diethylaminopropylamine, 2-dimethylaminoethylamine, 2-diethylaminoethylamine, 2-amino-1-ethoxycarbonylamido-ethane, 3-amino-1-ethoxycarbonylamido-propane, 4-amino-1-ethoxycarbonylamido-butane, 3-aminoquinuclidine, 2-[(phenylaminocarbonyl)amino]ethylamine, 2-[(phenylaminocarbonyl)amino]propylamine, 4-aminomethyl-piperidine, 4-(ethoxycarbonyl)aminoethyl-piperidine, N-methylpiperazine, 4-amino-1-carboxyethyl-piperidine, N,N-dimethylpropylidene-diamine, N,N-dimethylpropylidene-diamine, N,N-diethylethylidene-diamine, N,N-dimethylethylene-diamine, N-(2-aminoethyl)ethyl carbamate and N-(2-aminoethyl)propyl carbamate.

The halogen compounds of the general formulae (VII) and (XI) are known or can be prepared by known methods [Beilstein's Handbuch der organischen Chemie (Beilstein's Handbook of Organic Chemistry) 2, 197, 201, 250, 278; 3, 9, 10; 21, 461, 462, 463].

Halogen compounds which can be used, for example, according to the invention are: chloroacetonitrile, 2-chloropropionnitrile, 3-chlorobutyronitrile, 3-bromopropylphthalimide, 3-chloropropylphthalimide, 2-bromoethylphthalimide, 2-bromoethylphthalimide, 4-bromobutylphthalimide, 4-chlorobutylphthalimide, chloroacetyldiethylamide, chloroacetyldimethylamide, methyl chloroacetate, ethyl chloroacetate, ethyl bromoacetate, methyl bromoacetate, 2-δ-bromobutyl-1,2-benzoisothiazol-3(2H)-one-1,1-dioxide and 2-γ-bromopropyl-1,2-benzoisothiazol-3(2H)-one-1,1-dioxide.

The carbonyl compounds of the general formulae (VIII) and (XII) employed as starting substances are known or can be prepared by known methods [Beilstein's Handbuch der organischen Chemie (Beilstein's Handbook of Organic Chemistry) −1, 594, 629, 662].

Aldehydes which can be used, for example, according to the invention are: acetaldehyde, propionaldehyde, butyraldehyde and benzaldehyde.

The compounds according to the invention can be used as active compounds in medicaments. The substances according to the invention have a particularly high affinity for cerebral 5-hydroxy-tryptamine receptors of the 5-HT$_1$ type. These are connected with agonistic, partial agonistic or antagonistic actions on the serotonin receptor. In comparison to the structurally related known compounds, they surprisingly exhibit a larger therapeutic range.

The high-affinity ligands for the serotonin-1 receptor described in the present invention thus represent active compounds for combating diseases which are characterized by disturbances of the serotoninergic system, in particular with the involvement of receptors which possess high affinity for 5-hydroxytryptamine (5-HT$_1$ type). They are therefore suitable for the treatment of disorders of the central nervous system such as anxiety, tension and depression states, sexual dysfunctions caused by the central nervous system, sleep disturbances, and for the treatment of cognitive deficits for the improvement of learning and memory capacities and for the treatment of Alzheimer's disease. Furthermore, these active compounds are also suitable for the modulation of the cardiovascular system. They also intervene in the regulation of the cerebral circulation and thus represent effective agents for combating migraine. They are also suitable for the prophylaxis and combating of the consequences of cerebral infarct events (Apoplexia cerebri) such as stroke or cerebral ischaemia. The compounds according to the invention can likewise be employed for combating pain conditions. They are also suitable for combating disorders of the intestinal tract which are characterized by disturbances of the serotoninergic system and also by disturbances of the carbohydrate metabolism.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound is in each case present in a concentration from about 0.5 to 90% by weight of the total mixture, i.e. in amounts which are sufficient to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used, if desired, as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, argillacious earths, talc, chalk), ground synthetic minerals (for example highly disperse silica, silicates), sugars (for example sucrose, lactose and dextrose), emulsifiers (for example polyoxyethylene fatty acid esters), polyoxyethylene fatty alcohol ethers (for example lignin, sulphite waste liquors, methylcellulose, starch and polyvinylpyrrolidone) and lubricants (for example magnesium stearate, talc, stearic acid and sodium sulphate).

Administration takes place in a customary manner, preferably orally or parenterally, in particular perlingually or intravenously. In the case of oral administration, tablets can, of course, also contain additives, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tableting. In the case of aqueous suspensions, various flavor improvers or colorants can be added to the active compounds in addition to the abovementioned auxiliaries.

In the case of parenteral administration, solutions of the active compounds using suitable liquid excipients can be employed.

In general, it has proved advantageous on intravenous administration to administer amounts from about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this, it can sometimes be necessary to deviate from the amounts mentioned, depending on the body weight or the type of application route, on the individual behavior towards the medicament, the manner of its formulation and the point in time or interval at which administration takes place. Thus, in some cases it may be sufficient to manage with less than the previously mentioned minimum amount, whereas in other cases the upper limit mentioned must be exceeded. In the case of the administration of larger amounts, it may be advisable to divide these into a number of individual doses over the day.

Preparation examples

EXAMPLE 1

6-Methoxy-4-[4-(N-1,2-benzisothiazol-3(2H)-one-1,1-dioxide-yl)]-butylamino-1,3,4,5-tetrahydrobenz[c,d]indole hydrochloride

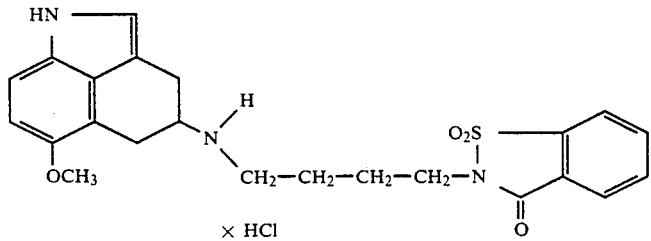

× HCl 2.5 g of 6-methoxy-4-1,3,4,5-tetrahydrobenz[c,d]-indole and 1.3 g of triethylamine are initially introduced in 50 ml of dimethylformamide. A solution of 2-(4-bromobutyl)-1,2-benzisothiazol-3(2H)-one-1,1-dioxide in 20 ml of dimethylformamide is added dropwise and the mixture is stirred for 4 hours at 50° C. It is then poured into water and extracted using methylene chloride. The crude product is chromatographed twice over silica gel 60 (40–63 μm) using ethyl acetate:ethanol 9:1. After the second chromatography, the clean fractions are combined, ethereal HCl is added and the solvent is stripped off at room temperature. The title compound is obtained as a hydrochloride in the form of a powder.

TLC: (silica gel 60) diisopropyl ether:ethanol 3:2
R$_f$: 0.458
Yield: 2.5 g (40.5% of theory).

EXAMPLE 2

4-[4-(N-1,2-Benzisothiazol-3(2H)-one-1,1-dioxide-yl)]-butylamino-1,3,4,5-tetrahydrobenz[c,d]indole

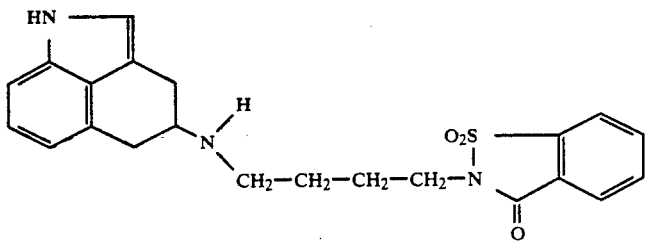

1.72 g of 4-amino-1,3,4,5-tetrahydrobenz[c,d]indole and 1.01 g of triethylamine are initially introduced in 40 ml of dimethylformamide. A solution of 3.18 g of 2-(4-bromobutyl)-1,2-benzisothiazol-3(2H)-one-1,1-dioxide in 15 ml of dimethylformamide is added dropwise and the mixture is stirred for 4 hours at 50° C. It is then poured into water and extracted using methylene chloride. The crude product is chromatographed over silica gel 60 (40–63 μm) using ethyl acetate:ethanol 9:1. The clean fractions are combined, ethereal hydrochloric acid is added, the solvent is stripped off and the substance is isolated as the hydrochloride in the form of a powder.

TLC: (silica gel 60) ethyl acetate:ethanol 9:1
$R_f$: 0.142
Yield: 2.35 g (52.7% of theory).

EXAMPLE 3

6-Methoxy-4-[4-(N-2,3-dihydro-1,2-benzisothiazol-1,1-dioxid-yl)]-butylamino-1,3,4,5-tetrahydrobenz[c,d]indole hydrochloride

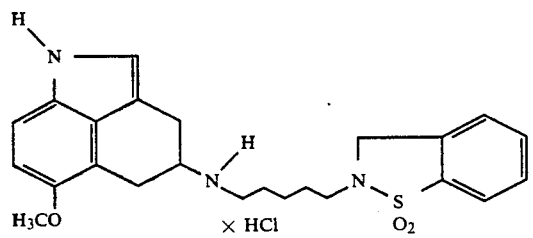

This compound was prepared in analogy to the procedure described in example 1 with 6-methoxy-4-amino-1,3,4,5-tetrahydrobenz[c,d]indole and 2-(4-bromobutyl)-2,3-dihydro-1,2-benzisothiazol-1,1-dioxid as starting materials.

M.p.: 234°–237° C.
TCC: (silica gel 60) toluene/methanol 7:3
$R_f$: 0.27
Yield: 29% of theory

EXAMPLE 4

6-Methoxy-4-[4-(N-4-fluorobenzenesulfonyl-N-methyl-)amidobutyl]-amino-1,3,4,5-tetrahydrobenz[c,d]indole hydrochloride

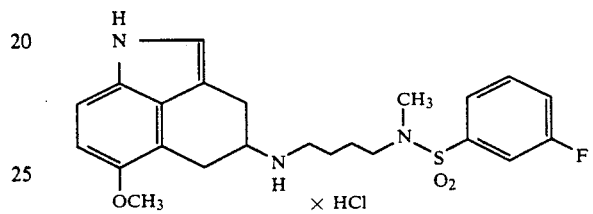

This compound was prepared in analogy to the procedure given in example 1 with 6-methoxy-4-amino-1,3,4,5-tetrahydrobenz[c,d]indole and N-methyl-N-(4-bromomethyl)-4-fluorobenzenesulfonamide as starting material.

M.p.: 168°–170° C.
TCC: (silica gel 60) toluene/methanol 7:3
$R_f$: 0.32
Yield: 36% of theory

EXAMPLE 5

6-Methoxy-4-[N-propyl-N-(ethyloxycarbonylaminoethyl)]amino-1,3,4,5-tetrahydrobenz[c,d]indole

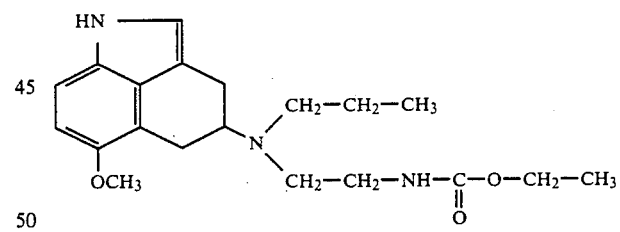

660 mg of 6-methoxy-4-[N-propyl-N-(aminoethyl)-]amino-1,3,4,5-tetrahydrobenz[c,d]indole are initially introduced in 25 ml of methylene chloride. 5 ml of a 50% strength aqueous potassium carbonate solution are added. A solution of 236 μl of ethyl chloroformate and 5 ml of methylene chloride are added dropwise at 0° C. with vigorous stirring. The mixture is stirred for 1 hour at 0° C. It is diluted with water and the phases are separated. The aqueous phase is extracted once more using methylene chloride. The organic phases are combined, dried over sodium sulphate and filtered. 1.5 g of activated carbon are added to the solution and the mixture is stirred for 2 hours at room temperature. It is then filtered and the filtrate is evaporated. The substance is obtained as a viscous resin.

TLC: (silica gel 60) diisopropyl ether:ethanol 3:2
$R_f$: 0.606

Yield: 540 mg (64% of theory)

EXAMPLE 6

6-Methoxy-4-[N-propyl-N-(methylsulphonylamidoethyl)]-amino-1,3,4,5-tetrahydrobenz[c,d]indole

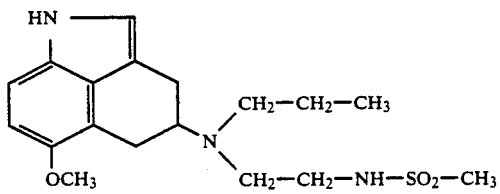

1.14 g of 6-methoxy-4-[N-propyl-N-(aminoethyl)]-amino-1,3,4,5-tetrahydrobenz[c,d]indole and 553 mg of potassium carbonate are initially introduced in 40 ml of methylene chloride. A solution of 550 mg of methanesulphonyl chloride and 5 ml of methylene chloride is added dropwise at room temperature and the mixture is stirred for 4 hours at room temperature. It is then diluted with water, and the organic phase is separated off and evaporated. The residue is chromatographed over silica gel 60 (40–63 μm) using cyclohexane:ethyl acetate 1:1. The oil obtained is crystallized using petroleum ether/diisopropyl ether. Colorless crystals are obtained.

m.p.: 118° C.
TLC: (silica gel 60) diisopropyl ether:ethanol 3:2
$R_f$: 0.617
Yield: 930 mg (63.7% of theory)

EXAMPLE 7

6-Methoxy-4-[N-propyl-N-(methylsulphonylamidoethyl)]-amino-1,3,4,5-tetrahydrobenz[c,d]indole

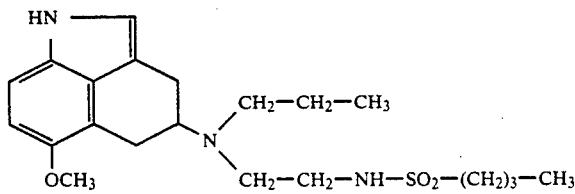

1.15 g of 6-methoxy-4-[N-propyl-N-(aminoethyl)]-amino-1,3,4,5-tetrahydrobenz[c,d]indole and 553 mg of potassium carbonate are initially introduced in 40 ml of methylene chloride. 752 mg of butanesulphonyl chloride are added dropwise at room temperature and the mixture is stirred for 4 h at room temperature. It is then diluted with water, and the organic phase is separated off and evaporated. The residue is chromatographed over silica gel 60 (40–63 μm) using cyclohexane:ethyl acetate 1:1. The compound is obtained as a viscous resin.

TLC: (silica gel 60) cyclohexane:ethyl acetate 1:1
$R_f$: 0.767
Yield: 1.24 g (76.1% of theory).

EXAMPLE 8

6-Methoxy-4-[N-propyl-N-(tosylamidoethyl)]-amino-1,3,4,5-tetrahydrobenz[c,d]indole hydrochloride

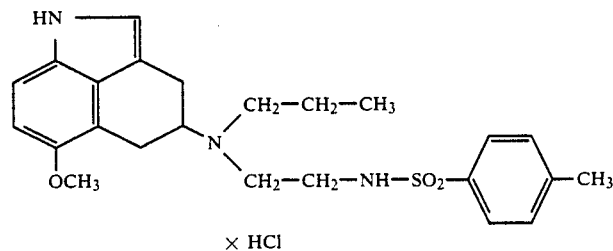

2.32 g of 6-methoxy-4-[4-propyl-N-(aminoethyl)]-amino-1,3,4,5-tetrahydrobenz[c,d]indole are initially introduced in 45 ml of methylene chloride with 4.5 ml of 50% strength potassium carbonate solution. A solution of 1.7 g of tosyl chloride and 15 ml of methylene chloride is added dropwise at room temperature with vigorous stirring. The mixture is stirred for 3 hours at room temperature. It is then diluted using water and methylene chloride, the phases are separated and the organic phase is evaporated. The residue is chromatographed over silica gel 60 (40–63 μm) using diisopropyl ether:ethanol 3:2.

The oil obtained is dissolved in diethyl ether and ethereal hydrochloric acid is added. The solvent is stripped off and the hydrochloride in the form of a powder is dried in a high vacuum at 50° C.

TLC: (silica gel 60) diisopropyl ether:ethanol 3:2
$R_f$: 0.708
Yield: 2 g (52% of theory).

EXAMPLE 9

6-Methoxy-4-[N-propyl-N-(naphthylsulphonylamidoethyl)]-amino-1,3,4,5-tetrahydrobenz[c,d]indole hydrochloride

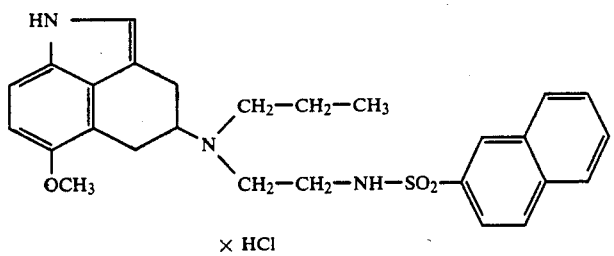
× HCl 862 g of 6-methoxy-4-[N-propyl-N-(aminoethyl)]-amino-1,3,4,5-tetrahydrobenz[c,d]indole are initially introduced in 15 ml of methylene chloride with 1.5 ml of 50% potassium carbonate solution. A solution of 748 mg of 2-naphthalenesulphonyl chloride and 5 ml of methylene chloride is added dropwise at room temperature. The mixture is stirred overnight at room temperature, then diluted using water and methylene chloride and the organic phase is separated off. The crude product is chromatographed over silica gel 60 (40–63 μm) using cyclohexane: ethyl acetate 1:1. The product is dissolved in ethyl acetate. The salt is then precipitated using ethereal hydrochloric acid. The mixture is diluted using ether and filtered with solution. The compound is obtained as the hydrochloride in the form of a powder.

TLC: cyclohexane:ethyl acetate 1:1
$R_f$: 0.307
Yield: 910 mg (59.1% of theory).

EXAMPLE 10

6-Methoxy-4-[N-propyl-N-(phenylureidoethyl)]-amino-1,3,4,5-tetrahydrobenz[c,d]indole

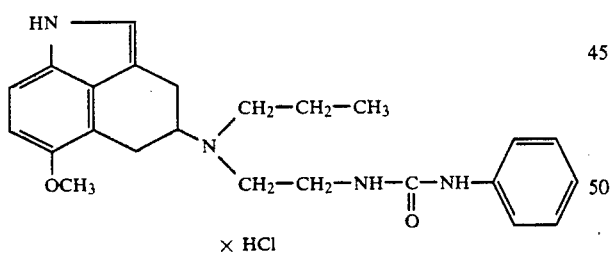
× HCl 1.18 g of 6-methoxy-4-[N-propyl-N-(aminoethyl)]-amino-1,3,4,5-tetrahydrobenz[c,d]indole are initially introduced in 20 ml of methylene chloride. A few drops of triethylamine are added and 420 mg of phenyl isocyanate are then added dropwise at room temperature. The mixture is stirred overnight at room temperature and evaporated. The residue is chromatographed over silica gel 60 (40–63 μm) using ethyl acetate:ethanol 9:1. The residue is dissolved in diethyl ether and the salt is precipitated using ethereal hydrochloric acid.

The substance is obtained as the hydrochloride in the form of a powder.

TLC: (silica gel 60) ethyl acetate:ethanol 9:1
$R_f$: 0.176
Yield: 760 mg (42% of theory).

EXAMPLE 11

6-Methoxy-4-[N-propyl-N-(aminoethyl)]-amino-1,3,4,5-tetrahydrobenz[c,d]indole

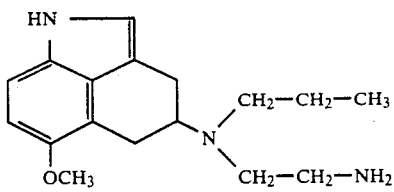

3.44 g of lithium aluminum hydride are initially introduced in 50 ml of absolute diethyl ether and the mixture is heated to reflux. A solution of 6.4 g of 6-methoxy-4-[N-propyl-N-(cyanomethyl)]-amino-1,3,4,5-tetrahydrobenz[c,d]indole in 75 ml of absolute diethyl ether is added dropwise and the mixture is stirred for 4 hours under reflux. It is then cautiously decomposed using water and filtered with suction. The residue is boiled twice with ethyl acetate. The organic phases are combined and evaporated. The product can be crystallized from the oily residue using petroleum ether:diisopropyl ether. A colourless powder is obtained.

m.p.: 146°–147° C.
Yield: 4.6 g (70.8% of theory).

EXAMPLE 12

6-Methoxy-4-[N-propyl-N-(cyanomethyl)]-amino-1,3,4,5-tetrahydrobenz[c,d]indole

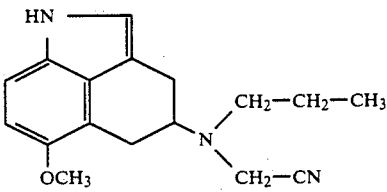

7.2 g of 6-methoxy-4-propylamino-1,3,4,5-tetrahydrobenz[c,d]indole are brought to reaction in 150 ml of methyl ethyl ketone at 70° C. with 11.5 g of chloroacetonitrile nitrile in the presence of 20.7 g of potassium carbonate and 1 g of potassium iodide. The reaction is complete after 3.5–4 hours. The mixture is filtered and evaporated. The crude product is chromatographed over silica gel 60 (63–200 μm) using cyclohexane:ethyl acetate 1:1. The substance is obtained as a viscous oil.

TLC: (silica gel 60) cyclohexane:ethyl acetate 1:1
$R_f$: 0.447
Yield: 8 g (94% of theory)

EXAMPLE 13

6-Methoxy-4-propylamino-1,3,4,5-tetrahydrobenz[c,d]indole

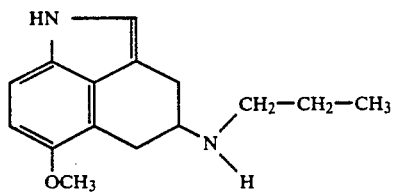

1.25 g of 6-methoxy-4-amino-1,3,4,5-tetrahydrobenz[c,d]indole are initially introduced in 40 ml of methanol. 265 µl of glacial acetic acid and 492 mg of sodium cyanoborohydride are added and the mixture is heated to 60° C. 440 µl of propionaldehyde are added dropwise at this temperature during the course of 30 min. The mixture is stirred for 1 h at 60° C. and then evaporated. The residue is taken up in methylene chloride and washed once with water. The organic phase is evaporated, and the residue is taken up in ethyl acetate and stirred for 10 min with 5 molar sodium hydroxide solution. The organic phase is separated off, extracted once more using ethyl acetate and evaporated. The residue is chromatographed over silica gel 60 (40-63 µm) using diisopropyl ether:ethanol 3:2. The product is a viscous oil.

TLC: (silica gel 60) diisopropyl ether:ethanol 3:2
R$_f$: 0.204
Yield: 800 mg (53% of theory)

EXAMPLE 14

6-Methoxy-4-(dimethylsulphamoylethyl)-amino-1,3,4,5-tetrahydrobenz[c,d]indole

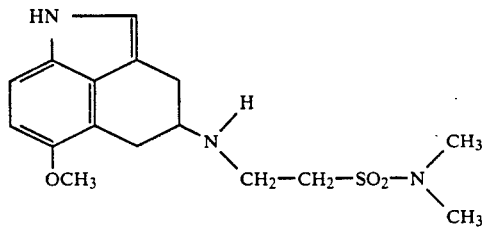

1 g of 6-methoxy-4-oxo-1,3,4,5-tetrahydrobenz[c,d]indole are initially introduced in 30 ml of methanol with 5 g of molecular sieve (4 Å). 2.3 g of acetic acid are added and the mixture is cooled to 0° C. 1.14 g of 2-dimethylsulphamoylethylamine are added and the mixture is stirred for 30 minutes at 0° C. It is allowed to come to room temperature and 1.3 g of sodium cyanoborohydride are added and the mixture is stirred for 4 hours at room temperature. It is then filtered and evaporated. The residue is taken up in ethyl acetate, 20% strength sodium hydroxide solution is added and the mixture is stirred for 15 min. The phases are separated, and the aqueous phase is washed with ethyl acetate and the combined organic phases are evaporated. The residue is chromatographed over silica gel 60 (40-63 µm) using diisopropylamine:ethanol 4:1 as eluent. The substance is obtained as a viscous oil.

TLC: (silica gel 60) ethyl acetate:ethanol 9:1
R$_f$: 0.189
Yield: 400 mg (24% of theory)

EXAMPLE 15

6-Methoxy-4-[N-propyl-N-(dimethylsulphamoylethyl)]-amino-1,3,4,5-tetrahydrobenz[c,d]indole

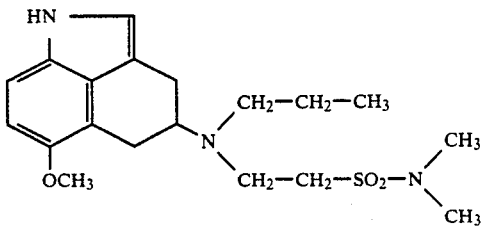

362 mg of 6-methoxy-4-(dimethylsulphamoylethyl)-amino-1,3,4,5-tetrahydrobenz[c,d]indole are initially introduced in 7.5 ml of methanol. 480 mg of glacial acetic acid and 93 mg of propionaldehyde are added. 270 mg of sodium cyanoborohydride are then added and the mixture is stirred for 2 h at room temperature. After evaporating, the residue is taken up in ethyl acetate, 20% strength sodium hydroxide solution is added and the mixture is stirred for 10 minutes. The ethyl acetate phase is separated off and extracted using 3 N hydrochloric acid. The hydrochloric acid phase is rendered alkaline and extracted a number of times using ethyl acetate. The organic phase is evaporated and chromatographed over silica gel 60 (63-200 µm) using ethyl acetate. The product obtained is again chromatographed over silica gel 60 (63-200 µm) using a cyclohexane/ethyl acetate gradient with the addition of a little triethylamine. The product obtained is dissolved in ether and the hydrochloride is precipitated using ethereal hydrochloric acid. A colorless hydroscopic solid is obtained.

TLC: (silica gel 60) ethyl acetate
R$_f$: 0.466
Yield: 125 mg (28.1% of theory).

EXAMPLE 16

6-Methoxy-4-(methylsulphonylamidopropyl)]-amino-1,3,4,5-tetrahydrobenz[c,d]indole hydrochloride

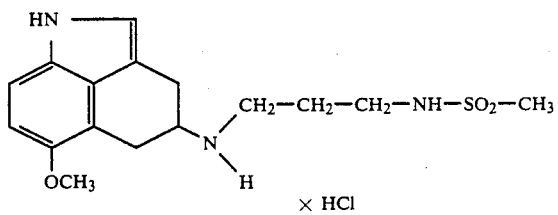

500 mg of palladium-carbon (10% strength) are prehydrogenated in 20 ml of methanol and 5 ml of methanol/hydrochloric acid (1 mol×1$^{-1}$). A solution of 1.2 g of 6-methoxy-4-[N-benzyl-N-(methylsulphonylamidopropyl)]-amino-1,3,4,5-tetrahydrobenz[c,d]indole in 40 ml of methanol is added and the mixture is hydrogenated until hydrogen uptake is complete. The solution is filtered from the catalyst, neutralized and evaporated. The residue is chromatographed over silica gel 60 (40-63 µm) using ethyl acetate:ethanol 9:1. The clean fractions are combined, ethereal hydrochloric acid is added and the solvent is stripped off at room temperature. The compound is obtained as the hydrochloride in the form of a powder.

EXAMPLE 17

6-Methoxy-4-[N-propyl-N-(methylsulphonylamidopropyl)]-amino-1,3,4,5-tetrahydrobenz[c,d]indole

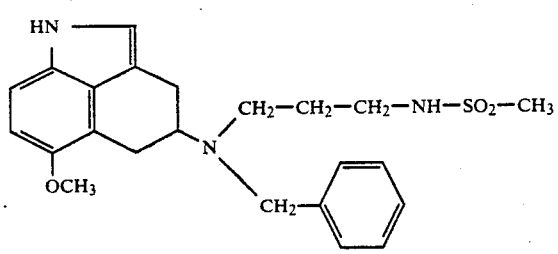

1.7 g of 6-methoxy-4-[N-benzyl-N-(aminopropyl)]-amino-1,3,4,5-tetrahydrobenz[c,d]indole and 672 mg of potassium carbonate are initially introduced in 50 ml of methylene chloride. A solution of 613 mg of methanesulphonyl chloride and 10 ml of methylene chloride is added dropwise at room temperature and the mixture is stirred overnight at room temperature. The precipitate is then filtered off and the solution is concentrated on a rotary evaporator. The residue is chromatographed over silica gel 60 (840–63μm) using cyclohexane:ethyl acetate 1:1.

Crystals of m.p.: 132°–133° C. are obtained.

TLC: (silica gel 60) cyclohexane:ethyl acetate 1:1
$R_f$: 0.182
Yield: 1.2 g (57.7% of theory)

EXAMPLE 18

6-Methoxy-4-(4-fluorophenylsulphonylamidopropyl)-amino-1,3,4,5-tetrahydrobenz[c,d]indole hydrochloride

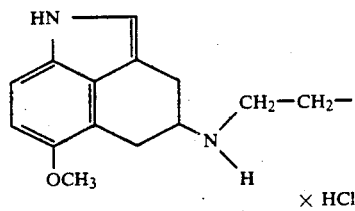

800 mg of palladium-carbon (10% strength) are prehydrogenated in 25 ml of methanol and 6.5 ml of methanol/hydrochloric acid (1 mol×1⁻¹). A solution of 1.6 g of 6-methoxy-4-[N-benzyl-N-(4-fluorophenylsulphonylamidopropyl)]-amino-1,3,4,5-tetrahydrobenz[c,d]indole in 25 ml of methanol is added and the mixture is hydrogenated until hydrogen uptake is complete. The solution is filtered off from the catalyst, neutralized and evaporated. The residue is chromatographed over silica gel 60 (40–63 μm) using ethyl acetate:ethanol 9:1. The product is taken up in ether and the salt is precipitated using ethereal hydrochloric acid.

TLC: (silica gel 60) diisopropyl ether:ethanol 3:2
$R_f$: 0.481
Yield: 840 mg (58.7% of theory)

EXAMPLE 19

6-Methoxy-4-[N-benzyl-N-(4-fluorophenylsulphonylamidopropyl)]-amino-1,3,4,5-tetrahydrobenz[c,d]indole

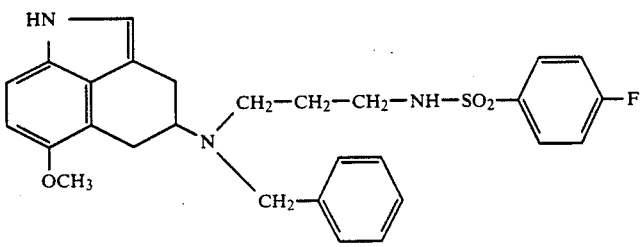

12.5 g of 6-methoxy-4-[-N-benzyl-N-(aminopropyl)]-amino-1,3,4,5-tetrahydrobenz[c,d]indole and 470 mg of potassium carbonate are initially introduced in 30 ml of methylene chloride. A solution of 730 mg of 4-fluorobenzenesulphonyl chloride in 5 ml of methylene chloride is added dropwise at room temperature and the mixture is stirred overnight at room temperature. It is then diluted using water and methylene chloride, and the organic phase is separated off and evaporated. The crude product is chromatographed over silica gel 60 (40–63 μm) using cyclohexane:ethyl acetate 7:3. The substance is obtained as a viscous resin.

TLC: (silica gel 60) cyclohexane:ethyl acetate 7:3
$R_f$: 0.172
Yield: 12.5 g (72.5% of theory)

EXAMPLE 20

6-Methoxy-4-N-benzyl-N-aminopropyl)-amino-1,3,4,5-tetrahydrobenz[c,d]indole

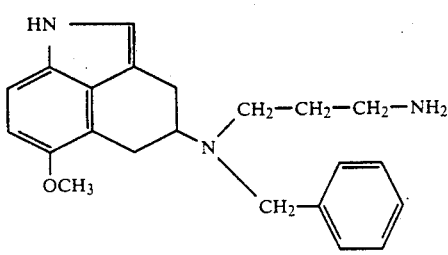

882 mg of lithium aluminum hydride are initially introduced in 15 ml of absolute diethyl ether under argon. A suspension of 2 g of 6-methoxy-4-[N-benzyl-N-(2-cyanoethyl)-amino-1,3,4,5-tetrahydrobenz[c,d]indole in 50 ml of absolute diethyl ether is added dropwise under reflux. The mixture is stirred for 4 hours under reflux and then cooled to room temperature. It is decomposed using 8 ml of ethyl acetate, 1 ml of water and 2 ml of 15% strength potassium hydroxide solution. The mixture is filtered with suction and the residue is washed three times with ethyl acetate. The mother liquor is evaporated and the residue obtained is chromatographed over silica gel 60 (40–63 μm) using methanol:triethylamine 95:5. The substance is obtained as a viscous oil.

TLC: (silica gel 60) methanol:triethylamine 95:5
$R_f$: 0.186
Yield: 1.35 g (66.5% of theory).

EXAMPLE 21

6-Methoxy-4-[N-benzyl-N-(2-cyanoethyl)]-amino-1,3,4,5-tetrahydrobenz[c,d]indole

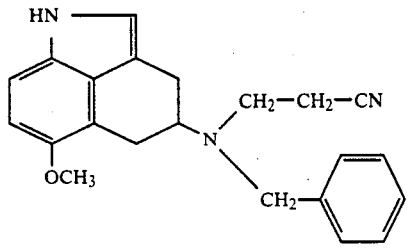

2.05 g of 6-methoxy-4-benzylamino-1,3,4,5-tetrahydrobenz[c,d]indole and 1.86 g of acrylonitrile and 25 mg of copper(II) acetate are stirred under reflux for 12 hours. The reaction mixture is chromatographed over silica gel 60 (63–200 μm) using cyclohexane:ethyl acetate 7:3. A colourless powder of melting point 126° C. is obtained.

TLC: (silica gel 60) cyclohexane:ethyl acetate 1:1
$R_f$: 0.445
Yield: 2.05 g (84.7% of theory)

EXAMPLE 22

6-Methoxy-4-benzylamino-1,3,4,5-tetrahydrobenz[c,-d]indole

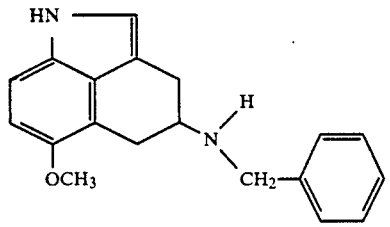

2 g of 6-methoxy-4-amino-1,3,4,5-tetrahydrobenz[c,-d]indole are initially introduced in 75 ml of methanol. 450 μl of acetic acid and 800 mg of sodium cyanoborohydride are added, the mixture is heated to 60° C. and 1.12 g of benzaldehyde are added dropwise during the course of 30 minutes. The mixture is stirred for 1 hour at 60° C. and then evaporated. The residue is taken up in ethyl acetate and stirred for 10 minutes with 20% strength sodium hydroxide solution. The organic phase is separated off and evaporated. The residue is dissolved in methylene chloride, activated carbon is added and the mixture is stirred for 1 hour at room temperature. The solution is filtered and evaporated. The brown crystals obtained are chromatographed over silica gel 60 (40–63 μm) using ethyl acetate:ethanol 9:1.

A crystalline powder of m.p.: 143°–144° C. is obtained.

TLC: ethyl acetate:ethanol 9:1
$R_f$: 0.359
Yield: 2.95 g (70.2% of theory).

Use Example

EXAMPLE 23

Affinity for the 5-HT$_1$ receptor

The high affinity of the compounds according to the invention for 5-hydroxytryptamine receptors of the subtype 1 is represented by way of example in Table 1. The values indicated are data which have been determined from receptor binding studies with calf hippocampus membrane preparations. 3H-Serotonin was used for this as a radioactively labelled ligand.

TABLE 1

| Compound of Example No. | Ki (nmol/l) |
|---|---|
| 1 | 2 |
| 2 | 2 |
| 5 | 1 |
| 6 | 6 |
| 8 | 1 |
| 9 | 2 |
| 15 | 8 |
| 18 | 0.7 |

Furthermore, the antidepressive action properties of the compounds were investigated. For this, the influence of the compounds on the so-called "behavioral despair" behavior was investigated according to Porsolt et al. Arch. Int. Pharmacodyn. Ther. 229, 327 (1977). By way of example, the compounds according to Examples 3, 4, 7 and 13 show positive action.

It is understood that the specification and examples are illustrative but not limitative of the present invention and that other embodiments within the spirit and scope of the invention will suggest themselves to those skilled in the art.

We claim:

1. A 1,3,4,5-tetrahydrobenz[c,d]indole of the formula

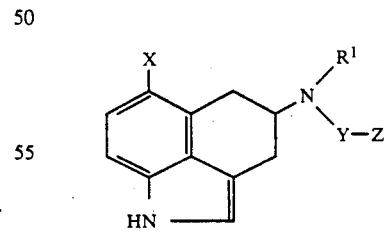

in which
$R^1$ stands for H, $C_1$–$C_4$-alkyl or benzyl,
X stands for H, $OCH_3$, OH, $SCH_3$, F, Cl, Br, CN or $CONH_2$,
Y stands for a straight-chain or branched, saturated or unsaturated alkylene chain having up to 6 carbon atoms
and
Z stands for cyano or for a group of the formula

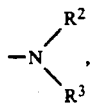

—SO$_2$NR$^7$R$^8$ or —CONR$^7$R$^8$ wherein

R$^7$ and R$^8$ are identical or different, and stand for hydrogen, lower alkyl, phenyl, benzyl or phenethyl, R$^2$ and R$^3$ are identical or different and stand for hydrogen, lower alkyl, phenyl or benzyl where the phenyl radicals can be substituted by fluorine, chlorine, bromine, lower alkyl, lower alkoxy or trifluoromethyl, or stand for a group of the formula —COR$^9$ or —SO$_2$R$^{10}$, wherein R$^9$ denotes hydrogen or a group NHR$^{11}$, or denotes lower alkyl or lower alkoxy, or denotes phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl each of which is optionally substituted by lower alkyl, lower alkoxy, fluorine, chlorine, bromine, trifluoromethyl, dimethylamino or diethylamino, R$^{10}$ denotes lower alkyl which is optionally substituted by cyano, fluorine, chlorine, bromine, trifluoromethyl or lower alkoxycarbonyl, or denotes phenyl, naphthyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl each of which is optionally substituted by lower alkyl, lower alkoxy, fluorine, chlorine, bromine, trifluoromethyl, dimethylamino or diethylamino, or denotes a group NR$^7$R$^8$, where R$^7$ and R$^8$ have the abovementioned meaning, and R$^{11}$ denotes lower alkyl which is optionally substituted by cyano, fluorine, chlorine or bromine, or denotes phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl each of which is optionally substituted by lower alkyl, lower alkoxy, fluorine, chlorine, bromine, trifluoromethyl, dimethylamino or diethylamino, or R$^2$ and R$^3$, together with the nitrogen atom, form a heterocyclic ring from the group consisting of

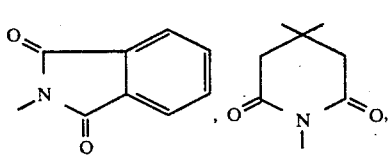

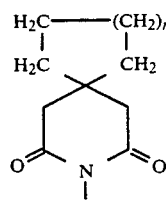

-continued

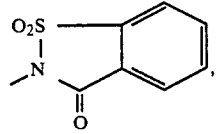

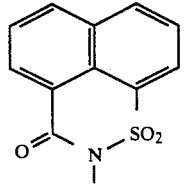

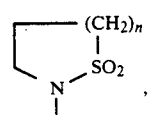

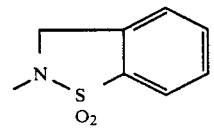

wherein n denotes a number 1 or 2, or a salt thereof.

2. A 1,3,4,5-tetrahydrobenz[c,d]indole according to claim 1, in which

R$^1$ stands for hydrogen, methyl, ethyl, n-propyl or benzyl

X stands for H, OCH$_3$, OH, SCH$_3$, F, Cl, CN or CONH$_2$,

Y stands for a straight-chain alkylene chain having 2 to 4 carbon atoms and

Z stands for Cyano or for a group of the formula

SO$_2$NR$^7$R$^8$ CONR$^7$R$^8$ where

R$^7$ and R$^8$ are identical or different and stand for hydrogen, methyl, ethyl, propyl, isopropyl, butyl, isobutyl or tert.butyl, R$^2$ and R$^3$ are identical or different, and stand for hydrogen, methyl, ethyl, propyl, isopropyl, butyl, isobutyl, tert.butyl or stand for phenyl which is optionally substituted by fluorine, chlorine, methyl or methoxy, or for a group —COR$^9$ or —SO$_2$R$^{10}$, wherein R$^9$ denotes hydrogen or a group NHR$^{11}$, or denotes methyl, ethyl, propyl, isopropyl, methoxy, ethoxy, propoxy, isopropoxy, or phenyl, benzyl, benzyloxy, thienyl, furyl, pyridyl, pyrimidyl, quinolyl or isoquinolyl each of which is optionally substituted by methyl, methoxy, fluorine or chlorine, R$^{10}$ denotes methyl, ethyl, propyl, isopropyl, butyl or isobutyl each of which is optionally substituted by fluorine, chlorine, methoxycarbonyl, ethoxycarbonyl, propoxycarbonyl, isopropoxycarbonyl, butoxycarbonyl or isobutoxycarbonyl, or denotes phenyl, naphthyl, benzyl, thienyl, furyl, pyridyl, pyrimidyl, quinolyl or isoquinolyl each of which is optionally substituted by methyl, ethyl, propyl, isopropyl, methoxy, fluorine or chlorine, or denotes a group $NR^7R^8$, where $R^7$ and $R^8$ have the abovementioned meaning, and $R^{11}$ denotes methyl, ethyl, propyl, isopropyl, butyl, isobutyl, pentyl, isopentyl, hexyl or isohexyl each of which is optionally substituted by fluorine or chlorine, or denotes phenyl or benzyl each of which can be substituted by fluorine, chlorine, methyl or methoxy, or $R^2$ and $R^3$, together with the nitrogen atom, form a heterocyclic ring from the group consisting of

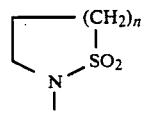 , 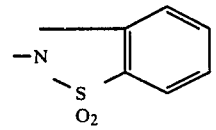

wherein n denotes a number 1 or 2, or a salt thereof.

3. A compound according to claim 1, wherein such compound is 6-methoxy-4-[4-(N-1,2-benzisothiazol-3(2H)-one-1,1-dioxide-yl)]-butylamino-1,3,4,5-tetrahydrobenz[c,d]indole of the formula

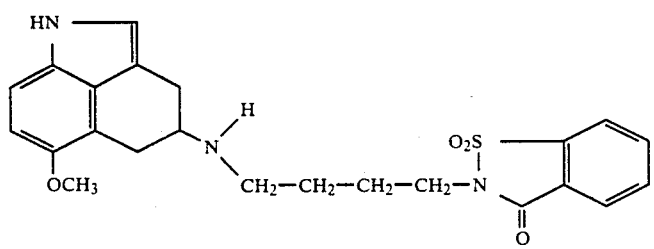

or a salt thereof.

4. A compound according to claim 1, wherein such compound is 4-[4-(N-1,2-benzisothiazol-3(2H)-one-1,1-dioxide-yl)]-butylamino-1,3,4,5-tetrahydrobenz[c,d]indole of the formula

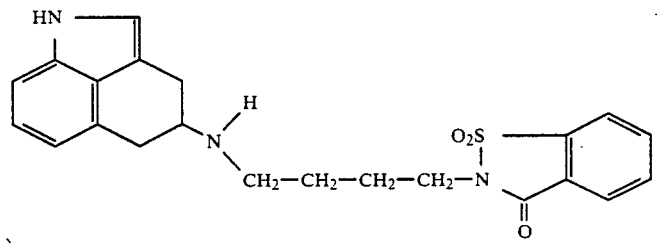

or a salt thereof.

5. A compound according to claim 1, wherein such compound is 6-methoxy-4-[N-propyl-N-(ethyloxycarbonylaminoethyl)]-amino-1,3,4,5-tetrahydrobenz[c,-d]indole of the formula

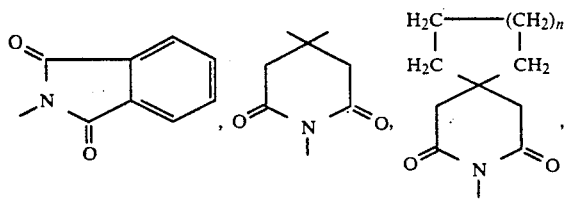

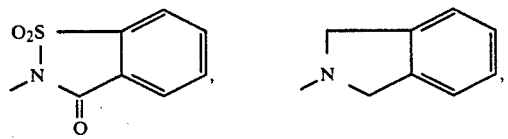

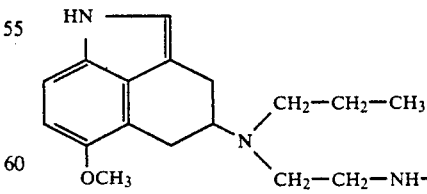

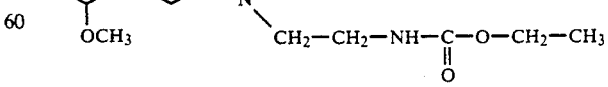

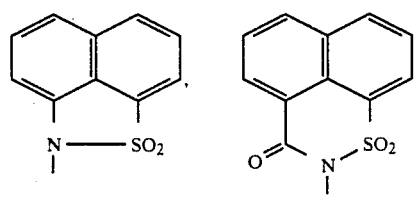

and or a salt thereof.

6. A compound according to claim 1, wherein such compound is 6-methoxy-4-[N-propyl-N-(methylsulphonylamidoethyl)]-amino-1,3,4,5-tetrahydrobenz[c,-d]indole of the formula

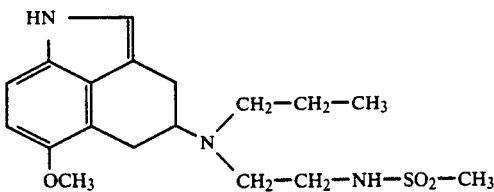

or a salt thereof.

7. A compound according to claim 1, wherein such compound is 6-methoxy-4-[N-propyl-N-(tosylamidoethyl)]-amino-1,3,4,5-tetrahydrobenz[c,d]indole of the formula

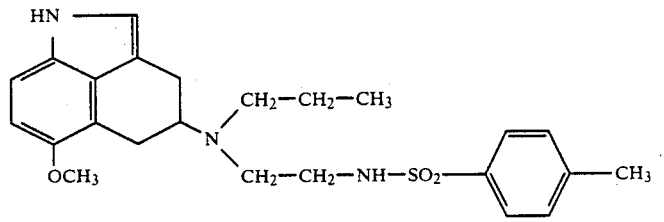

or a salt thereof.

8. A compound according to claim 1, wherein such compound is 6-methoxy-4-[N-propyl-N-(2-naphthylsulphonylamidoethyl)]-amino-1,3,4,5-tetrahydrobenz[c,-d]indole of the formula

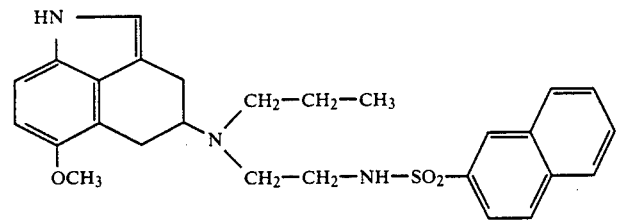

or a salt thereof.

9. A compound according to claim 1, wherein such compound is 6-methoxy-4-[N-propyl-N-(dimethylsulphamoylethyl)]-amino-1,3,4,5-tetrahydrobenz[c,d]indole of the formula

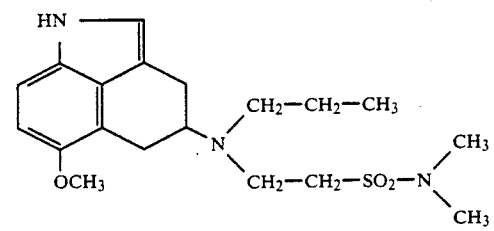

or a salt thereof.

10. A compound according to claim 1, wherein such compound is 6-methoxy-4-(4-fluorophenylsulphonylamidopropyl)-amino-1,3,4,5-tetrahydrobenz[c,-d]indole of the formula

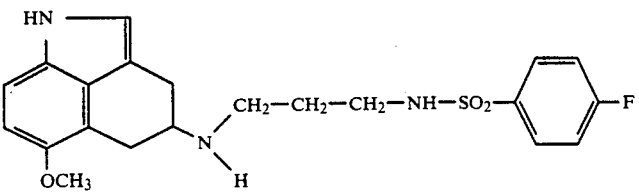

or a salt thereof.

11. A composition for treating a disorder of the central nervous system, cardiovascular system or cerebral circulation comprising an amount effective therefor of a compound or salt thereof of claim 1 and a diluent.

12. A composition according to claim 11 in the form of a tablet, capsule or ampule.

13. A method of treating depression which comprises administering to such patient an amount effective therefor of a compound or salt thereof of claim 1.

14. The method according to claim 13, wherein such compound is
6-methoxy-4-[4-(N-1,2-benzisothiazol-3(2H)-one-1,1-dioxide-yl)]-butylamino-1,3,4,5-tetrahydrobenz[c,-d]indole, 4-[4-(N-1,2-benzisothiazol-3(2H)-one-1,1-dioxide-yl)]-butylamino-1,3,4,5-tetrahydrobenz[c,d]indole,
6-methoxy-4-[N-propyl-N-(ethyloxycarbonylaminoethyl)]-amino-1,3,4,5-tetrahydrobenz[c,d]indole,
6-methoxy-4-[N-propyl-N-(methylsulphonylamidoethyl)]-amino-1,3,4,5-tetrahydrobenz[c,d]indole,
6-methoxy-4-[N-propyl-N-(tosylamidoethyl)]-amino-1,3,4,5-tetrahydrobenz[c,d]indole,
6-methoxy-4-[N-propyl-N-(2-naphthylsulphonylamidoethyl)]-amino-1,3,4,5-tetrahydrobenz[c,d]indole,
6-methoxy-4-[N-propyl-N-(dimethylsulphamoylethyl)]-amino-1,3,4,5-tetrahydrobenz[c,d]indole or
6-methoxy-4-(4-fluorophenylsulphonylamidopropyl)-amino-1,3,4,5-tetrahydrobenz[c,d]indole,
or a salt thereof.

* * * * *

UNITED STATES PATENT AND TRADEMARK OFFICE
CERTIFICATE OF CORRECTION

PATENT NO. : 5,021,438
DATED : June 4, 1991
INVENTOR(S) : Junge et al.

It is certified that error appears in the above-identified patent and that said Letters Patent is hereby corrected as shown below:

Title Page     FOREIGN PATENT DOCUMENTS:   Delete " 3346513 " and substitute -- 3346573 --

Signed and Sealed this

Fourth Day of May, 1993

Attest:

MICHAEL K. KIRK

*Attesting Officer*     *Acting Commissioner of Patents and Trademarks*